(12) United States Patent
Bhardwaj et al.

(10) Patent No.: US 12,397,178 B2
(45) Date of Patent: Aug. 26, 2025

(54) WEARABLE FOCUSED PHASED ARRAY DEVICE FOR MODULATION

(71) Applicant: SecondWave Systems, Inc., State College, PA (US)

(72) Inventors: Anuj Bhardwaj, Austin, TX (US); Jeffrey Heyman, Somerville, MA (US); Mikel Langron, State College, PA (US); Kashyap Patel, Hoboken, NJ (US); Michael Whetzel, Port Matilda, PA (US)

(73) Assignee: SecondWave Systems, Inc., State College, PA (US)

( * ) Notice: Subject to any disclaimer, the term of this patent is extended or adjusted under 35 U.S.C. 154(b) by 341 days.

(21) Appl. No.: 17/922,492

(22) PCT Filed: May 3, 2021

(86) PCT No.: PCT/US2021/030464
§ 371 (c)(1),
(2) Date: Oct. 31, 2022

(87) PCT Pub. No.: WO2021/222892
PCT Pub. Date: Nov. 4, 2021

(65) Prior Publication Data
US 2023/0293910 A1      Sep. 21, 2023

Related U.S. Application Data

(60) Provisional application No. 63/018,599, filed on May 1, 2020.

(51) Int. Cl.
*A61N 7/00* (2006.01)
*B06B 1/02* (2006.01)

(52) U.S. Cl.
CPC .............. *A61N 7/00* (2013.01); *B06B 1/0215* (2013.01); *A61N 2007/0052* (2013.01);
(Continued)

(58) Field of Classification Search
CPC .............. A61N 7/00–02; B06B 1/0215; G10K 11/341–355
See application file for complete search history.

(56) References Cited

U.S. PATENT DOCUMENTS

| 3,236,240 A | 2/1966 | Bradley |
| 6,508,774 B1 | 1/2003 | Acker et al. |

(Continued)

FOREIGN PATENT DOCUMENTS

| WO | 2020068473 A1 | 4/2020 |
| WO | 2020185734 A1 | 9/2020 |
| WO | 2021188200 A2 | 9/2021 |

OTHER PUBLICATIONS

Cotero, Victoria, et al. "Noninvasive sub-organ ultrasound stimulation for targeted neuromodulation." Nature Communications 10.1 (2019): 952.*

(Continued)

*Primary Examiner* — Carolyn A Pehlke
(74) *Attorney, Agent, or Firm* — The Webb Law Firm

(57) ABSTRACT

Devices for providing an acoustic wave to a target location include at least one transducer device and at least one beam-forming processor to cause the at least one transducer device to produce a first acoustic wave, the first acoustic wave includes a plurality of pulses having a pulse repetition frequency, where a pulse width of each pulse is in a range of 10 ns to 10 μs and the pulse repetition frequency is in a range of 1 Hz to 50 Hz, receive data associated with a second acoustic wave, wherein the second acoustic wave is a reflection of the first acoustic wave, determine a character- (Continued)

istic of the second acoustic wave, and determine whether to change a beam path of an acoustic wave produced by the at least one transducer device based on the characteristic of the second acoustic wave. Methods and computer program products are also disclosed.

18 Claims, 19 Drawing Sheets

(52) U.S. Cl.
CPC ............... *A61N 2007/0078* (2013.01); *A61N 2007/0095* (2013.01); *B06B 2201/76* (2013.01)

(56) References Cited

U.S. PATENT DOCUMENTS

| | | | |
|---|---|---|---|
| 7,382,082 B2 | 6/2008 | Bhardwaj | |
| 7,791,253 B2 | 9/2010 | Bhardwaj | |
| 8,382,672 B2 * | 2/2013 | Andrews | A61B 8/4477 600/459 |
| 2006/0167500 A1 | 7/2006 | Towe et al. | |
| 2008/0194952 A1 | 8/2008 | Luo et al. | |
| 2011/0150924 A1 | 6/2011 | Della Rocca et al. | |
| 2011/0178441 A1 | 7/2011 | Tyler | |
| 2013/0150756 A1 * | 6/2013 | Vitek | A61B 8/5207 601/2 |
| 2015/0148878 A1 | 5/2015 | Yoo et al. | |
| 2017/0046010 A1 | 2/2017 | Losh | |
| 2017/0205500 A1 | 7/2017 | Kiyose | |
| 2017/0312548 A1 | 11/2017 | Patil et al. | |
| 2019/0030375 A1 | 1/2019 | Zachar | |
| 2019/0160309 A1 | 5/2019 | Ebbini et al. | |
| 2020/0254283 A1 * | 8/2020 | Bae | G16H 40/63 |
| 2021/0346725 A1 * | 11/2021 | Rousso | A61B 8/085 |

OTHER PUBLICATIONS

Austeng et al., "The impact of "non-half-wavelength" element spacing on sparse array optimization", Department of Informatics, 4 pages, University of Oslo.

Gao et al., "Diagnostic utility of clinical laboratory data determinations for patients with the severe COVID-19", Journal of Medical Virology, 2020, pp. 791-796, vol. 92.

Huang et al., "Clinical features of patients infected with 2019 novel coronavirus in Wuhan, China", Lancet, Feb. 15, 2020, pp. 497-506, vol. 395.

Mehta et al., "COVID-19: consider cytokine storm syndromes and immunosuppression", Lancet, Mar. 28, 2020, pp. 1033-1034, vol. 395.

* cited by examiner

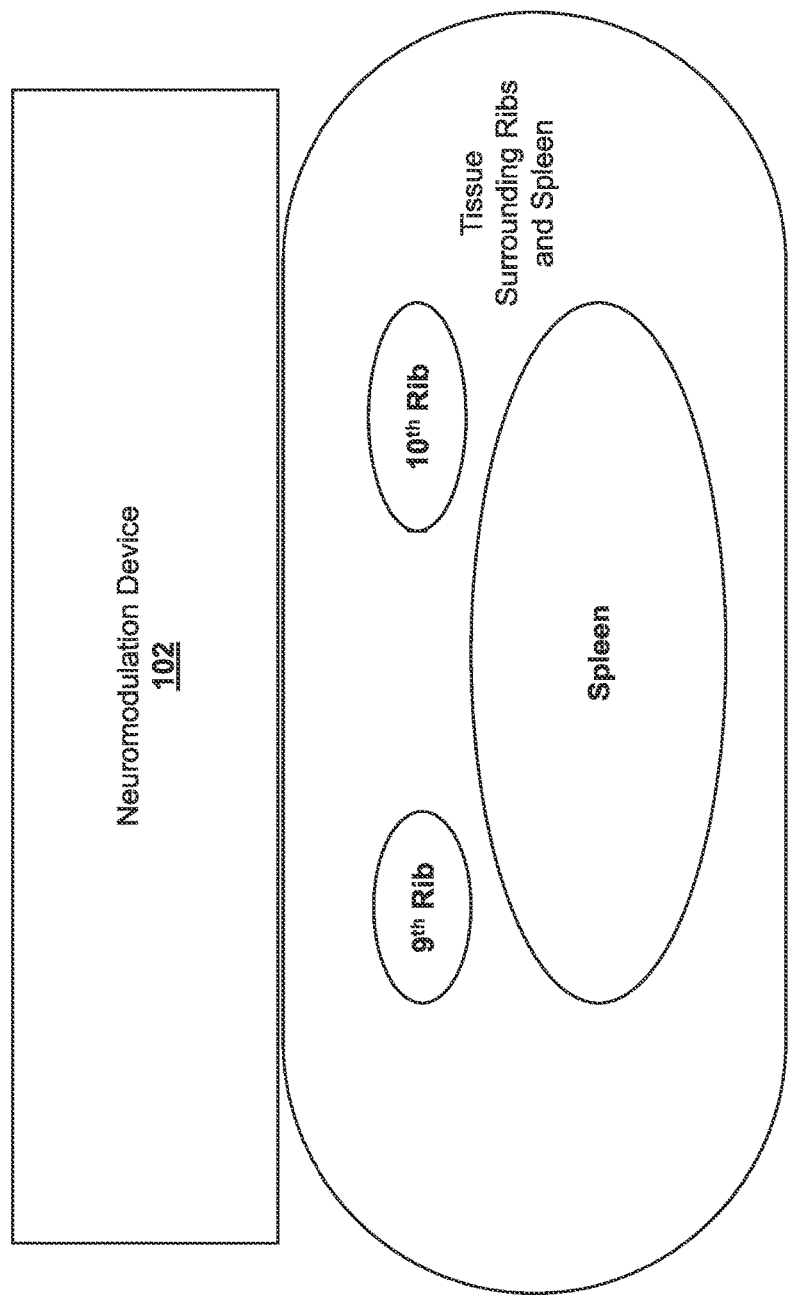

WEARABLE FOCUSED PHASED ARRAY DEVICE FOR MODULATION

CROSS REFERENCE TO RELATED APPLICATIONS

This application is the United States national phase of International Application No. PCT/US2021/030464, filed May 3, 2021, and claims priority to U.S. Provisional Patent Application No. 63/018,599, filed May 1, 2020, the disclosures of which are hereby incorporated by reference in their entirety.

This invention was made with Government support under Contract No. 140D6318C0067 dated Jul. 5, 2018 and as amended by Amendment of Solicitation/Modification No. P00003, awarded by Defense Advanced Research Projects Agency (DARPA). The Government has certain rights in the invention.

BACKGROUND

Field

The present disclosure relates to ultrasound devices and use of the same for treating patients. More particularly, the present disclosure relates to phased array ultrasound devices and uses of the same for treating various ailments and conditions in patients.

Technical Considerations

The coronavirus disease 2019 (COVID-19) carries a high mortality rate. In severe cases, hyperinflammation is caused by a "cytokine storm" that leads to respiratory failure known as acute respiratory distress syndrome (ARDS). It is estimated that 50-60% of these patients will die.

Today, no treatment exists to prevent or treat ARDS although the condition has been linked to an increase in certain pro-inflammatory cytokines. For example, COVID-19 patients produce higher concentrations of specific cytokines, including IL-1$\beta$, IL-7, IL-8, IL-10, GCSF, IFN-$\gamma$, and TNF-$\alpha$. Clinical therapies that can suppress these pro-inflammatory cytokines may be capable of treating patients, such as those with severe cases of COVID-19, to calm this cytokine storm and prevent death. However, existing anti-inflammatory treatments primarily consist of expensive drugs and biologics with significant side effects. Therefore, a need exists in the art for additional treatments for inflammatory conditions such as ARDS.

SUMMARY

Accordingly, disclosed are systems, methods, and computer program products for providing a treatment, such as an acoustic wave, to a target location.

Further embodiments or aspects are set forth in the following numbered clauses:

Clause 1: A device comprising: at least one transducer device, wherein the at least one transducer device comprises a material, wherein the material comprises: lead zirconate titanate (PZT); polyvinylidene difluoride (PVDF); aluminum nitride (AlN); scandium (Sc) doped AlN; or any combination thereof; wherein the at least one transducer device comprises: a gas matrix piezoelectric (GMP) array; a capacitive micro-machined acoustic transducer (cMUT) array; or a piezoelectric micro-machined ultrasound transducer (pMUT) array; and at least one beam-forming processor programmed or configured to: cause the at least one transducer device to produce a first acoustic wave, wherein the first acoustic wave comprises a plurality of pulses having a pulse repetition frequency, wherein a pulse width of each pulse of the plurality of pulses is in a range of 10 ns to 10 $\mu$s, and wherein the pulse repetition frequency is in a range of 1 Hz to 50 Hz; receive data associated with a second acoustic wave, wherein the second acoustic wave is an acoustic wave that is a reflection of the first acoustic wave; determine a characteristic of the second acoustic wave; and determine whether to change a beam path of an acoustic wave produced by the at least one transducer device based on the characteristic of the second acoustic wave.

Clause 2: The device of clause 1, wherein the first acoustic wave has a bandwidth of 20% to 150% of peak frequency, wherein the peak frequency is a range of 50 kHz to 5 MHz.

Clause 3: The device of clause 1 or clause 2, wherein a number of cycles per pulse width of a pulse of the first acoustic wave is in a range of 1 to 5.

Clause 4: The device of any of clauses 1-3, wherein the at least one processor is further programmed or configured to: generate an image based on the characteristic of the second acoustic wave.

Clause 5: The device of any of clauses 1-4, wherein the at least one processor is further programmed or configured to: provide an indication based on the characteristic of the second acoustic wave.

Clause 6: The device of any of clauses 1-5, wherein the indication comprises at least one of: an indication associated with discontinuing a treatment, an indication associated with improper placement of the at least one transducer device, an indication associated with a prompt for receiving a user input, or any combination thereof.

Clause 7: The device of any of clauses 1-6, wherein, when determining whether to change the beam path of an acoustic wave produced by the at least one transducer device, the at least one beam-forming processor is programmed or configured to: determine an amount of change to be made to the beam path of an acoustic wave produced by the at least one transducer device from the beam path of the first acoustic wave based on the characteristic of the second acoustic wave, or determine that no amount of change is to be made to the beam path of an acoustic wave produced by the at least one transducer device from the beam path of the first acoustic wave based on the characteristic of the second acoustic wave.

Clause 8: The device of any of clauses 1-7, wherein the at least one beam-forming processor is further programmed or configured to: cause the at least one transducer device to change the beam path of an acoustic wave produced by the at least one transducer device based on the amount of change of the beam path of an acoustic wave produced by the at least one transducer device from the beam path of the first acoustic wave.

Clause 9: The device of any of clauses 1-8, wherein the at least one beam-forming processor is further programmed or configured to: cause the at least one transducer device to produce a third acoustic wave along the beam path based on causing the at least one transducer device to change the beam path of an acoustic wave produced by the at least one transducer device, wherein the third acoustic wave comprises a plurality of pulses having a pulse repetition frequency, wherein each pulse has a pulse width in a range of 10 $\mu$s to 200 ms, and wherein the pulse repetition frequency is in a range of 25 Hz to 1000 Hz.

Clause 10: The device of any of clauses 1-9, wherein the third acoustic wave has a bandwidth of 1-70% of peak frequency, wherein the peak frequency is a range of 50 kHz to 5 MHz.

Clause 11: The device of any of clauses 1-10, wherein a number of cycles per pulse width of a pulse of the third acoustic wave is in a range of 5 to 500.

Clause 12: The device of any of clauses 1-11, wherein the at least one transducer device comprises a plurality of transducer elements, and wherein each transducer element of the plurality of transducer elements comprises: PZT; polyvinylidene fluoride; PVDF; or any combination thereof.

Clause 13: The device of any of clauses 1-12, wherein the at least one transducer device comprises a microelectronic mechanical systems (MEMS) transducer device.

Clause 14: The device of any of clauses 1-13, wherein the MEMS transducer device comprises a cMUT array or a pMUT array.

Clause 15: The device of any of clauses 1-14, wherein, when determining a characteristic of the second acoustic wave, the at least one beam-forming processor is programmed or configure to: determine a phase delay between the first acoustic wave and the second acoustic wave, where the phase delay is a difference in time between the first acoustic wave and the second acoustic wave; determine an amplitude of the second acoustic wave; and determine whether the amplitude of the second acoustic wave satisfies a threshold.

Clause 16: The device of any of clauses 1-15, wherein, when determining the amount of change of the beam path of the beam path of an acoustic wave produced by the at least one transducer device from the beam path of the first acoustic wave, the at least one beam-forming processor is further programmed or configured to: determine the amount of change of the beam path of an acoustic wave produced by the at least one transducer device from the beam path of the first acoustic wave based on the phase delay and determining whether the amplitude of the second acoustic wave satisfies the threshold.

Clause 17: The device of any of clauses 1-16, wherein the at least one transducer device is an energy delivery transducer device, and wherein the device further comprises: a detection transducer device.

Clause 18: The device of any of clauses 1-17, wherein the energy receiving transducer device is configured to: receive the second acoustic wave; and provide the data associated with the second acoustic wave to the at least one beam-forming processor.

Clause 19: The device of any of clauses 1-18, wherein the at least one transducer device comprises a pMUT array, and wherein the pMUT array comprises: PZT; AlN; Sc doped AlN; or any combination thereof.

Clause 20: The device of any of clauses 1-19, further comprising: a pulser board assembly, wherein the pulser board assembly comprises: a printed circuit board (PCB); wherein the at least one transducer device and the at least one beam-forming processor are coupled to the PCB.

Clause 21: The device of any of clauses 1-20, wherein the pulser board assembly has a height in a range of 1 mm to 50 mm, a width in a range of 10 mm to 250 mm, and a length in a range of 10 mm to 250 mm.

Clause 22: The device of any of clauses 1-21, further comprising: a device to dissipate heat from the at least one transducer device and the at least one beam-forming processor; and wherein the device comprises a heat sink, a fan, and/or any combination thereof.

Clause 23: The device of any of clauses 1-22, further comprising: a material for coupling the device to a body of a user; wherein the material comprises an adhesive, a liquid-based acoustic coupling gel, and/or any combination thereof.

Clause 24: A method comprising: causing, with at least one beam-forming processor, at least one transducer device to produce a first acoustic wave, wherein the first acoustic wave comprises a plurality of pulses having a pulse repetition frequency, wherein a pulse width of each pulse of the plurality of pulses is in a range of 10 ns to 10 µs, and wherein the pulse repetition frequency is in a range of 1 Hz to 50 Hz; receiving, with the at least one-beam-forming processor, data associated with a second acoustic wave, wherein the second acoustic wave is an acoustic wave that is a reflection of the first acoustic wave; determine, with the at least one beam-forming processor, a characteristic of the second acoustic wave; and determine, with the at least one beam-forming processor, whether to change a beam path of an acoustic wave produced by the at least one transducer device based on the characteristic of the second acoustic wave.

Clause 25: The method of clause 24, wherein the first acoustic wave has a bandwidth of 20% to 150% of peak frequency, wherein the peak frequency is a range of 50 kHz to 5 MHz.

Clause 26: The method of clause 24 or 25, wherein a number of cycles per pulse width of a pulse of the first acoustic wave is in a range of 1 to 5.

Clause 27: The method of any of clauses 24-26, further comprising: generating an image based on the characteristic of the second acoustic wave.

Clause 28: The method of any of clauses 24-27, further comprising: providing an indication based on the characteristic of the second acoustic wave.

Clause 29: The method of any of clauses 24-28, wherein the indication comprises at least one of: an indication associated with discontinuing a treatment, an indication associated with improper placement of the at least one transducer device, an indication associated with a prompt for receiving a user input, or any combination thereof.

Clause 30: The method of any of clauses 24-29, wherein determining whether to change the beam path of an acoustic wave produced by the at least one transducer device comprises: determining an amount of change to be made to the beam path of an acoustic wave produced by the at least one transducer device from the beam path of the first acoustic wave based on the characteristic of the second acoustic wave, or determining that no amount of change is to be made to the beam path of an acoustic wave produced by the at least one transducer device from the beam path of the first acoustic wave based on the characteristic of the second acoustic wave.

Clause 31: The method of any of clauses 24-30, further comprising: causing the at least one transducer device to change the beam path of an acoustic wave produced by the at least one transducer device based on the amount of change of the beam path of an acoustic wave produced by the at least one transducer device from the beam path of the first acoustic wave.

Clause 32: The method of any of clauses 24-31, further comprising: causing the at least one transducer device to produce a third acoustic wave along the beam path based on causing the at least one transducer device to change the beam path of an acoustic wave produced by the at least one transducer device, wherein the third acoustic wave comprises a plurality of pulses having a pulse repetition frequency, wherein each pulse has a pulse width in a range of 10 μs to 200 ms, and wherein the pulse repetition frequency is in a range of 25 Hz to 1000 Hz.

Clause 33: The method of any of clauses 24-32, wherein the third acoustic wave has a bandwidth of 1-70% of peak frequency, wherein the peak frequency is a range of 50 kHz to 5 MHz.

Clause 34: The method of any of clauses 24-33, wherein a number of cycles per pulse width of a pulse of the third acoustic wave is in a range of 5 to 500.

Clause 35: The method of any of clauses 24-34, wherein the at least one transducer device comprises a plurality of transducer elements, and wherein each transducer element of the plurality of transducer elements comprises: PZT; polyvinylidene fluoride; PVDF; or any combination thereof.

Clause 36: The method of any of clauses 24-35, wherein the at least one transducer device comprises a MEMS transducer device.

Clause 37: The method of any of clauses 24-36, wherein the MEMS transducer device comprises a cMUT array or a pMUT array.

Clause 38: The method of any of clauses 24-37, wherein determining a characteristic of the second acoustic wave comprises: determining a phase delay between the first acoustic wave and the second acoustic wave, where the phase delay is a difference in time between the first acoustic wave and the second acoustic wave; determining an amplitude of the second acoustic wave; and determining whether the amplitude of the second acoustic wave satisfies a threshold.

Clause 39: The method of any of clauses 24-38, wherein determining the amount of change of the beam path of the beam path of an acoustic wave produced by the at least one transducer device from the beam path of the first acoustic wave comprises: determining the amount of change of the beam path of an acoustic wave produced by the at least one transducer device from the beam path of the first acoustic wave based on the phase delay and determining whether the amplitude of the second acoustic wave satisfies the threshold.

Clause 40: The method of any of clauses 24-39, wherein the at least one transducer device is an energy delivery transducer device, and wherein the device further comprises: a detection transducer device.

Clause 41: The method of any of clauses 24-40, wherein the energy receiving transducer device is configured to: receive the second acoustic wave; and provide the data associated with the second acoustic wave to the at least one beam-forming processor.

Clause 42: The method of any of clauses 24-41, wherein the at least one transducer device comprises a pMUT array, and wherein the pMUT array comprises: PZT; AlN; Sc doped AlN; or any combination thereof.

Clause 43: The method of any of clauses 24-42, wherein the at least one transducer device further comprises: a pulser board assembly, wherein the pulser board assembly comprises: a PCB; wherein the at least one transducer device and the at least one beam-forming processor are coupled to the PCB.

Clause 44: The method of any of clauses 24-43, wherein the pulser board assembly has a height in a range of 1 mm to 50 mm, a width in a range of 10 mm to 250 mm, and a length in a range of 10 mm to 250 mm.

Clause 45: The method of any of clauses 24-44, wherein the at least one transducer device further comprises: a device to dissipate heat from the at least one transducer device and the at least one beam-forming processor; and wherein the device comprises a heat sink, a fan, and/or any combination thereof.

Clause 46: The method of any of clauses 24-45, wherein the at least one transducer device further comprises: a material for coupling the device to a body of a user; wherein the material comprises an adhesive, a liquid-based acoustic coupling gel, and/or any combination thereof.

Clause 47: A non-transitory computer-readable medium including one or more instructions that, when executed by at least one processor, cause the at least one processor to: cause at least one transducer device to produce a first acoustic wave, wherein the first acoustic wave comprises a plurality of pulses having a pulse repetition frequency, wherein a pulse width of each pulse of the plurality of pulses is in a range of 10 ns to 10 μs, and wherein the pulse repetition frequency is in a range 1 Hz to 50 Hz; receive data associated with a second acoustic wave, wherein the second acoustic wave is an acoustic wave that is a reflection of the first acoustic wave; determine a characteristic of the second acoustic wave; and determine whether to change a beam path of an acoustic wave produced by the at least one transducer device based on the characteristic of the second acoustic wave.

Clause 48: The non-transitory computer-readable medium of clause 47, wherein the first acoustic wave has a bandwidth of 20% to 150% of peak frequency, wherein the peak frequency is a range of 50 kHz to 5 MHz.

Clause 49: The non-transitory computer-readable medium of clause 47 or clause 48, wherein a number of cycles per pulse width of a pulse of the first acoustic wave is in a range of 1 to 5.

Clause 50: The non-transitory computer-readable medium of any of clauses 47-49, wherein the one or more instructions further cause the at least one processor to: generate an image based on the characteristic of the second acoustic wave.

Clause 51: The non-transitory computer-readable medium of any of clauses 47-50, wherein the one or more instructions further cause the at least one processor to: provide an indication based on the characteristic of the second acoustic wave.

Clause 52: The non-transitory computer-readable medium of any of clauses 47-51, wherein the indication comprises at least one of: an indication associated with discontinuing a treatment, an indication associated with improper placement of the at least one transducer device, an indication associated with a prompt for receiving a user input, or any combination thereof.

Clause 53: The non-transitory computer-readable medium of any of clauses 47-52, wherein the one or more instructions that cause the at least one processor to determine whether to change the beam path of an acoustic wave produced by the at least one transducer device cause the at least one processor to: determine an amount of change to be made to the beam path of an acoustic wave produced by the at least one transducer device from the beam path of the first acoustic wave based on the characteristic of the second acoustic wave, or determine that no amount of change is to be made to the beam path of an acoustic wave produced by the at least one transducer device from the beam path of the first acoustic wave based on the characteristic of the second acoustic wave.

Clause 54: The non-transitory computer-readable medium of any of clauses 47-53, wherein the one or more instructions further cause the at least one processor to: cause the at least one transducer device to change the beam path of an acoustic wave produced by the at least one transducer device based on the amount of change of the beam path of an acoustic wave produced by the at least one transducer device from the beam path of the first acoustic wave.

Clause 55: The non-transitory computer-readable medium of any of clauses 47-54, wherein the one or more instructions cause the at least one processor to: cause the at least one transducer device to produce a third acoustic wave along the beam path based on causing the at least one transducer device to change the beam path of an acoustic wave produced by the at least one transducer device, wherein the third acoustic wave comprises a plurality of pulses having a pulse repetition frequency, wherein each pulse has a pulse width in a range of 10 μs to 200 ms, and wherein the pulse repetition frequency is in a range of 25 Hz to 1000 Hz.

Clause 56: The non-transitory computer-readable medium of any of clauses 47-55, wherein the third acoustic wave has a bandwidth of 1-70% of peak frequency, wherein the peak frequency is a range of 50 kHz to 5 MHz.

Clause 57: The non-transitory computer-readable medium of any of clauses 47-56, wherein a number of cycles per pulse width of a pulse of the third acoustic wave is in a range of 5 to 500.

Clause 58: The non-transitory computer-readable medium of any of clauses 47-57, wherein the one or more instructions that cause the at least one processor to determine a characteristic of the second acoustic wave cause the at least one processor to: determine a phase delay between the first acoustic wave and the second acoustic wave, where the phase delay is a difference in time between the first acoustic wave and the second acoustic wave; determine an amplitude of the second acoustic wave; and determine whether the amplitude of the second acoustic wave satisfies a threshold.

Clause 59: The non-transitory computer-readable medium of any of clauses 47-58, wherein the one or more instructions that cause the at least one processor to determine the amount of change of the beam path of the beam path of an acoustic wave produced by the at least one transducer device from the beam path of the first acoustic wave cause the at least one processor to: determine the amount of change of the beam path of an acoustic wave produced by the at least one transducer device from the beam path of the first acoustic wave based on the phase delay and determining whether the amplitude of the second acoustic wave satisfies the threshold.

Clause 60: A method of modulating a patient's immune system, comprising: applying at least one transducer device to skin of the patient, the at least one transducer device comprising: a material, wherein the material comprises: PZT; PVDF; AlN; Sc doped AlN; or any combination thereof; wherein the at least one transducer device comprises: a GMP array; a cMUT array; or a pMUT array; and at least one beam-forming processor; and delivering, with the at least one transducer device, a plurality of acoustic waves to a target site within the patient's body, thereby modulating the patient's immune system.

Clause 61: The method of clause 60, wherein the target site is the patient's spleen.

Clause 62: The method of clause 60 or clause 61, wherein the at least one transducer device is a 64-channel phased array transducer.

Clause 63: The method of any of clauses 60-62, wherein the at least one transducer device is configured to focus the plurality of acoustic waves to a depth of about 1 mm to about 500 mm beneath the patient's skin.

Clause 64: The method according to any of clauses 60-63, wherein the at least one beam-forming processor is programmed or configured to: cause the at least one transducer device to produce a first acoustic wave, wherein the first acoustic wave comprises a plurality of pulses having a pulse repetition frequency, wherein a pulse width of each pulse of the plurality of pulses is in a range of 10 ns to 10 μs, and wherein the pulse repetition frequency is in a range of 1 Hz to 50 Hz; receive data associated with a second acoustic wave, wherein the second acoustic wave is an acoustic wave that is a reflection of the first acoustic wave; determine a characteristic of the second acoustic wave; determine whether to change a beam path of an acoustic wave produced by the at least one transducer device based on the characteristic of the second acoustic wave; cause the at least one transducer device to change the beam path of an acoustic wave produced by the at least one transducer device based on the amount of change of the beam path of an acoustic wave produced by the at least one transducer device from the beam path of the first acoustic wave; and cause the at least one transducer device to produce a third acoustic wave along the beam path based on causing the at least one transducer device to change the beam path of an acoustic wave produced by the at least one transducer device, wherein the third acoustic wave comprises a plurality of pulses having a pulse repetition frequency, wherein each pulse has a pulse width in a range of 10 μs to 200 ms, and wherein the pulse repetition frequency is in a range of 25 Hz to 1000 Hz.

Clause 65: The method of any of clauses 60-64, wherein the at least one transducer device is an energy delivery transducer device, and wherein the device further comprises: a detection transducer device.

Clause 66: The method of any of clauses 60-65, wherein the energy receiving transducer device is configured to: receive the second acoustic wave; and provide the data associated with the second acoustic wave to the at least one beam-forming processor.

Clause 67: The method of any of clauses 60-66, wherein the at least one transducer device comprises a plurality of transducer elements, and wherein each transducer element of the plurality of transducer elements comprises: PZT; polyvinylidene fluoride; PVDF; or any combination thereof.

Clause 68: The method of any of clauses 60-67, wherein the at least one transducer device comprises a MEMS transducer device.

Clause 69: The method of any of clauses 60-68, wherein the MEMS transducer device comprises a cMUT array or a pMUT array.

Clause 70: The method of any of clauses 60-69, wherein the plurality of acoustic waves comprise a plurality of pulses delivered with the following parameters: a frequency of between about 30 kHz and about 10 MHz; a peak negative acoustic pressure amplitude of about 100 kPa to about 10 MPa; a spatial peak average intensity of about 100 W/cm$^2$ to about 2,000 W/cm$^2$; and/or a duty cycle of about 0.01% to about 60%.

Clause 71: The method of any of clauses 60-70, wherein the plurality of acoustic waves comprise a plurality of pulses delivered at a frequency of about 50 kHz to about 2 MHz.

Clause 72: The method of any of clauses 60-71, wherein the plurality of acoustic waves are delivered for about 9 minutes to about 20 minutes.

Clause 73: The method of any of clauses 60-72, wherein delivering the plurality of acoustic waves to the target site within the patient's body modulates levels of one or more of IL-1β, IL-6, and TNF-α in the patient.

Clause 74: The method of any of clauses 60-73, wherein delivering the plurality of acoustic waves to the target site within the patient's body decreases levels of one or more of IL-1β, IL-6, and TNF-α in the patient.

Clause 75: The method of any of clauses 60-74, wherein the patient is infected with a coronavirus.

Clause 76: The method of any of clauses 60-75, wherein the coronavirus is SARS-CoV-2.

Clause 77: A method of modulating levels of one or more of IL-1β, IL-6, and TNF-α in a patient infected with a coronavirus, comprising: applying at least one transducer device to skin of the patient, the at least one transducer device comprising: a material, wherein the material comprises: PZT; PVDF; AlN; Sc doped AlN; or any combination thereof; wherein the at least one transducer device comprises: a GMP array; a cMUT array; or a pMUT array; and at least one beam-forming processor programmed or configured to: cause the at least one transducer device to produce a first acoustic wave, wherein the first acoustic wave comprises a plurality of pulses having a pulse repetition frequency, wherein a pulse width of each pulse of the plurality of pulses is in a range of 10 ns to 10 μs, and wherein the pulse repetition frequency is in a range of 1 Hz to 50 Hz; receive data associated with a second acoustic wave, wherein the second acoustic wave is an acoustic wave that is a reflection of the first acoustic wave; determine a characteristic of the second acoustic wave; determine whether to change a beam path of an acoustic wave produced by the at least one transducer device based on the characteristic of the second acoustic wave; cause the at least one transducer device to change the beam path of an acoustic wave produced by the at least one transducer device based on the amount of change of the beam path of an acoustic wave produced by the at least one transducer device from the beam path of the first acoustic wave; and cause the at least one transducer device to produce a third acoustic wave along the beam path based on causing the at least one transducer device to change the beam path of an acoustic wave produced by the at least one transducer device, wherein the third acoustic wave comprises a plurality of pulses having a pulse repetition frequency, wherein each pulse has a pulse width in a range of 10 μs to 200 ms, and wherein the pulse repetition frequency is in a range of 25 Hz to 1000 Hz; and delivering, with the at least one transducer device, a plurality of third acoustic waves to the patient's spleen, wherein the waves are delivered at a frequency of about 50 kHz to about 2 MHz, thereby modulating the levels of IL-1β, IL-6, and TNF-α within the patient.

Also provided herein is a method of modulating a patient's immune system, including the steps of applying an ultrasonic transducer device to skin of the patient, the ultrasonic transducer device having at least one processor; and at least one ultrasonic transducer in communication with the at least one processor, and delivering, with the device, a plurality of acoustic waves to a target site within the patient's body, thereby modulating the patient's immune system.

Also provided herein is a method of modulating levels of one or more of IL-1β, IL-6, and TNF-α in a patient infected with a coronavirus, including the steps of applying an ultrasonic transducer device to skin of the patient, the ultrasonic transducer device having at least one processor and an array comprising a plurality of ultrasonic transducers in communication with the at least one processor, wherein at least one of the plurality of ultrasonic transducers is configured to receive acoustic waves and to convert received acoustic waves to electrical signals, wherein the at least one processor is programmed or configured to, based on electrical signals received from the at least one ultrasonic transducer configured to receive acoustic waves, determine whether there are one or more obstructions between the at least one transducer and the target site and to adjust output of the one or more ultrasonic transducers to avoid the one or more obstructions, and delivering, with the device and based at least in part on the determination, a plurality of acoustic waves to the patient's spleen, wherein the waves are delivered at a frequency of about 400 kHz to about 500 kHz, thereby modulating the levels of IL-1β, IL-6, and TNF-α within the patient.

BRIEF DESCRIPTION OF THE DRAWINGS

Additional advantages and details are explained in greater detail below with reference to the exemplary embodiments that are illustrated in the accompanying schematic figures, in which:

FIGS. 10A-10D are diagrams of a non-limiting embodiment of an example implementation of a process (e.g., process 900) for providing an acoustic wave to a target location;

DETAILED DESCRIPTION

Figure 1:
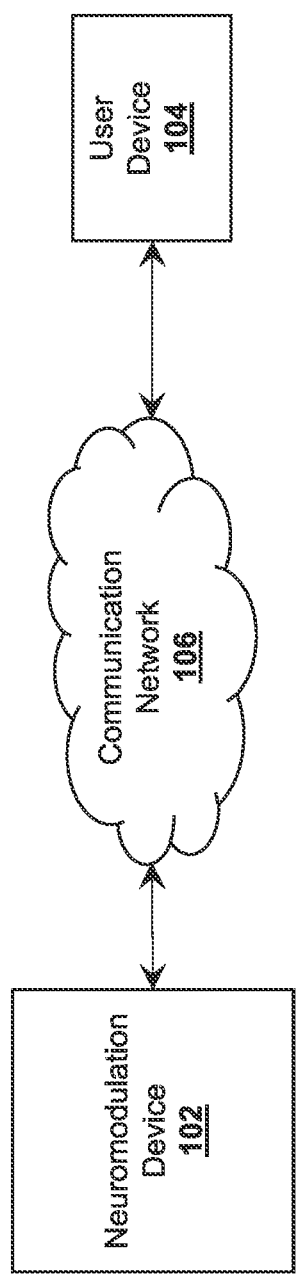
FIG. 1 is a diagram of a non-limiting embodiment or aspect of an environment in which systems, devices, products, apparatus, and/or methods, described herein, may be implemented according to the principles of the present disclosure.

For purposes of the description hereinafter, the terms "end," "upper," "lower," "right," "left," "vertical," "horizontal," "top," "bottom," "lateral," "longitudinal," and derivatives thereof shall relate to the disclosure as it is oriented in the drawing figures. However, it is to be understood that the disclosure may assume various alternative variations and step sequences, except where expressly specified to the contrary. It is also to be understood that the specific devices and processes illustrated in the attached drawings, and described in the following specification, are simply exemplary embodiments or aspects of the disclosure. Hence, specific dimensions and other physical characteristics related to the embodiments or aspects of the embodiments disclosed herein are not to be considered as limiting unless otherwise indicated.

No aspect, component, element, structure, act, step, function, instruction, and/or the like used herein should be construed as critical or essential unless explicitly described as such. In addition, as used herein, the articles "a" and "an" are intended to include one or more items and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise. The phase "based on" may also mean "in response to" where appropriate.

Embodiments of the present disclosure may include a modulation device for providing an acoustic wave to a target location that includes at least one transducer device, wherein the at least one transducer device comprises a material, wherein the material comprises: lead zirconate titanate (PZT); polyvinylidene difluoride (PVDF); aluminum nitride (AlN); scandium (Sc) doped AlN; or any combination thereof; wherein the at least one transducer device comprises: a gas matrix piezoelectric (GMP) array; a polymer-matrix piezocomposite array; a capacitive micro-machined acoustic transducer (cMUT) array; or a piezoelectric micro-machined ultrasound transducer (pMUT) array; and at least one beam-forming processor programmed or configured to: cause the at least one transducer device to produce a first acoustic wave, wherein the first acoustic wave comprises a plurality of pulses having a pulse repetition frequency, wherein a pulse width of each pulse of the plurality of pulses is in a range of 10 ns to 10 µs, and wherein the pulse repetition frequency is in a range of 1 Hz to 50 Hz; receive data associated with a second acoustic wave, wherein the second acoustic wave is an acoustic wave that is a reflection of the first acoustic wave; determine a characteristic of the second acoustic wave; and determine whether to change a beam path of an acoustic wave produced by the at least one transducer device based on the characteristic of the second acoustic wave. In some non-limiting embodiments, the first acoustic wave has a bandwidth of 20% to 150% of peak frequency, wherein the peak frequency is a range of 50 kHz to 5 MHz. In some non-limiting embodiments, a number of cycles per pulse width of a pulse of the first acoustic wave is in a range of 1 to 5. In some non-limiting embodiments, the at least one processor is further programmed or configured to: generate an image based on the characteristic of the second acoustic wave. In some non-limiting embodiments, the at least one processor is further programmed or configured to: provide an indication based on the characteristic of the second acoustic wave. In some non-limiting embodiments, the indication comprises at least one of: an indication associated with discontinuing a treatment, an indication associated with improper placement of the at least one transducer device, an indication associated with a prompt for receiving a user input, or any combination thereof. In some non-limiting embodiments, when determining whether to change the beam path of an acoustic wave produced by the at least one transducer device, the at least one beam-forming processor is programmed or configured to: determine an amount of change to be made to the beam path of an acoustic wave produced by the at least one transducer device from the beam path of the first acoustic wave based on the characteristic of the second acoustic wave, or determine that no amount of change is to be made to the beam path of an acoustic wave produced by the at least one transducer device from the beam path of the first acoustic wave based on the characteristic of the second acoustic wave. In some non-limiting embodiments, the at least one beam-forming processor is further programmed or configured to: cause the at least one transducer device to change the beam path of an acoustic wave produced by the at least one transducer device based on the amount of change of the beam path of an acoustic wave produced by the at least one transducer device from the beam path of the first acoustic wave. In some non-limiting embodiments, the at least one beam-forming processor is further programmed or configured to: cause the at least one transducer device to produce a third acoustic wave along the beam path based on causing the at least one transducer device to change the beam path of an acoustic wave produced by the at least one transducer device, wherein the third acoustic wave comprises a plurality of pulses having a pulse repetition frequency, wherein each pulse has a pulse width in a range of 10 µs to 200 ms, and wherein the pulse repetition frequency is in a range of 25 Hz to 1000 Hz. In some non-limiting embodiments, the third acoustic wave has a bandwidth of 1-70% of peak frequency, wherein the peak frequency is a range of 50 kHz to 5 MHz. In some non-limiting embodiments, a number of cycles per pulse width of a pulse of the third acoustic wave is in a range of 5 to 500. In some non-limiting embodiments, the at least one transducer device comprises a plurality of transducer elements, and wherein each transducer element of the plurality of transducer elements comprises: PZT; polyvinylidene fluoride; PVDF; or any combination thereof. In some non-limiting embodiments, the at least one transducer device comprises a MEMS transducer device. In some non-limiting embodiments, the MEMS transducer device comprises a cMUT array or a pMUT array. In some non-limiting embodiments, when determining a characteristic of the second acoustic wave, the at least one beam-forming processor is programmed or configured to: determine a phase delay between the first acoustic wave and the second acoustic wave, where the phase delay is a difference in time between the first acoustic wave and the second acoustic wave; determine an amplitude of the second acoustic wave; and determine whether the amplitude of the second acoustic wave satisfies a threshold. In some non-limiting embodiments, when determining the amount of change of the beam path of the beam path of an acoustic wave produced by the at least one transducer device from the beam path of the first acoustic wave, the at least one beam-forming processor is further programmed or configured to: determine the amount of change of the beam path of an acoustic wave produced by the at least one transducer device from the beam path of the first acoustic wave based on the phase delay and determining whether the amplitude of the second acoustic wave satisfies the threshold. In some non-limiting embodiments, the at least one transducer device is an energy delivery transducer device, and wherein the device further comprises: a detection transducer device. In some non-limiting embodiments, the energy receiving transducer device is configured to: receive the second acoustic wave; and provide the data associated with the second acoustic wave to the at least one beam-forming processor. In some non-limiting embodiments, the at least one transducer device comprises a pMUT array, and wherein the pMUT array comprises: PZT; AlN; Sc doped AlN; or any combination thereof. In some non-limiting embodiments, the modulation device further comprises: a pulser board assembly, wherein the pulser board assembly comprises: a PCB; wherein the at least one transducer device and the at least one beam-forming processor are coupled to the PCB. In some non-limiting embodiments, the pulser board assembly has a height in a range of 1 mm to 50 mm, a width in a range of 10 mm to 250 mm, and a length in a range of 10 mm to 250 mm. In some non-limiting embodiments, the modulation device further comprises: a device to dissipate heat from the at least one transducer device and the at least one beam-forming processor; and wherein the device comprises a heat sink, a fan, and/or any combination thereof. In some non-limiting embodiments, the modulation device further comprises: a material for coupling the device to a body of a user; wherein the material comprises an adhesive, a liquid-based acoustic coupling gel, and/or any combination thereof.

In this way, the modulation device provides a treatment for inflammatory conditions, such as ARDS. In addition, the modulation device provides an accurate way of delivering acoustic waves to a targeted location of a body of a user.

Referring now to FIG. 1, FIG. 1 is a diagram of an example environment 100 in which devices, systems, methods, and/or products described herein may be implemented. As shown in FIG. 1, environment 100 includes modulation device 102, user device 104, and communication network 106. In some non-limiting embodiments, modulation device 102 and user device 104 may interconnect (e.g., establish a connection to communicate, establish a communication connection, etc.) via wired connections, wireless connections, or a combination of wired and wireless connections.

Modulation device 102 may include one or more devices configured to provide acoustic waves (e.g., ultrasonic waves, ultrasonic beams, etc.) to a body of a user. For example, modulation device 102 may include appropriate electrical circuit components, such as a transducer and a processor to control the transducer. In some non-limiting embodiments, modulation device 102 may be sized and configured to be wearable on the body of a user. For example, modulation device 102 may have a wearable form-factor that allows for modulation device 102 to be placed upon and/or adhered to a body of a patient (e.g., a torso of a patient) for a period of time. In some non-limiting embodiments, modulation device 102 may have the following dimensions, including a length in a range of 60 to 250 mm, a width in a range of 40 to 250 mm, and a height in a range of 15 to 50 mm. In one example, modulation device 102 may have the following dimensions a length of 75 mm, a width of 55 mm, and a height of 19 mm. In some non-limiting embodiments, modulation device 102 may include a power source that is carried on board. For example, modulation device 102 may include a battery having a capacity in a range of 50 to 900,000 mAh.

In some non-limiting embodiments, modulation device 102 may include a 32-channel phased transducer array, which may be capable of providing an equivalent of 128-channel beam forming capability for high resolution focusing by mirroring the phased transducer array design on two different axes. In such an example, modulation device 102 may provide a peak frequency at 400 kHz and channel spacing at 1.5 mm, which may be equivalent to less than half of an ultrasonic wavelength in water and provides the ability to steer and focus an acoustic wave by avoiding energy loss due to side lobe generation. In some non-limiting embodiments, modulation device 102 may include circuitry and a transducer device capable of steering and focusing an acoustic wave with center focus conditions with target depths between 1 and 500 mm, steering conditions with target depths between 1 and 500 mm, and steering angles between 0 and 90 degrees in a volumetric space.

User device 104 may include one or more devices configured to be in communication with modulation device 102 via communication network 106. For example, user device 104 may include a desktop computer (e.g., a client device that communicates with a server) and/or the like. User device 104 may be configured to transmit data to and/or receive data from modulation device 102 via a short-range wireless communication connection (e.g., an NFC communication connection, an RFID communication connection, a Bluetooth® communication connection, and/or the like). In some non-limiting embodiments or aspects, user device 104 may be associated with a user of (e.g., a patient) of modulation device 102 or an individual (e.g., a medical practitioner) administering a treatment with modulation device 102. In some non-limiting embodiments, user device 104 may include an interface (e.g., a graphical user interface (GUI)) that allows for selection of operational features for control (e.g., only control) of modulation device 102 based on an application (e.g., a computer application, a mobile application, etc.).

Communication network 106 may include one or more wired and/or wireless networks. For example, communication network 106 may include a cellular network (e.g., a long-term evolution (LTE) network, a third generation (3G) network, a fourth generation (4G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, and/or the like, and/or a combination of some or all of these or other types of networks.

The number and arrangement of devices shown in FIG. 1 are provided as an example. There may be additional devices, fewer devices, different devices, or differently arranged devices than those shown in FIG. 1. Furthermore, two or more devices shown in FIG. 1 may be implemented within a single device, or a single device shown in FIG. 1 may be implemented as multiple devices. Additionally or alternatively, a set of devices of environment 100 may perform one or more functions described as being performed by another set of devices of environment 100.

Figure 2:
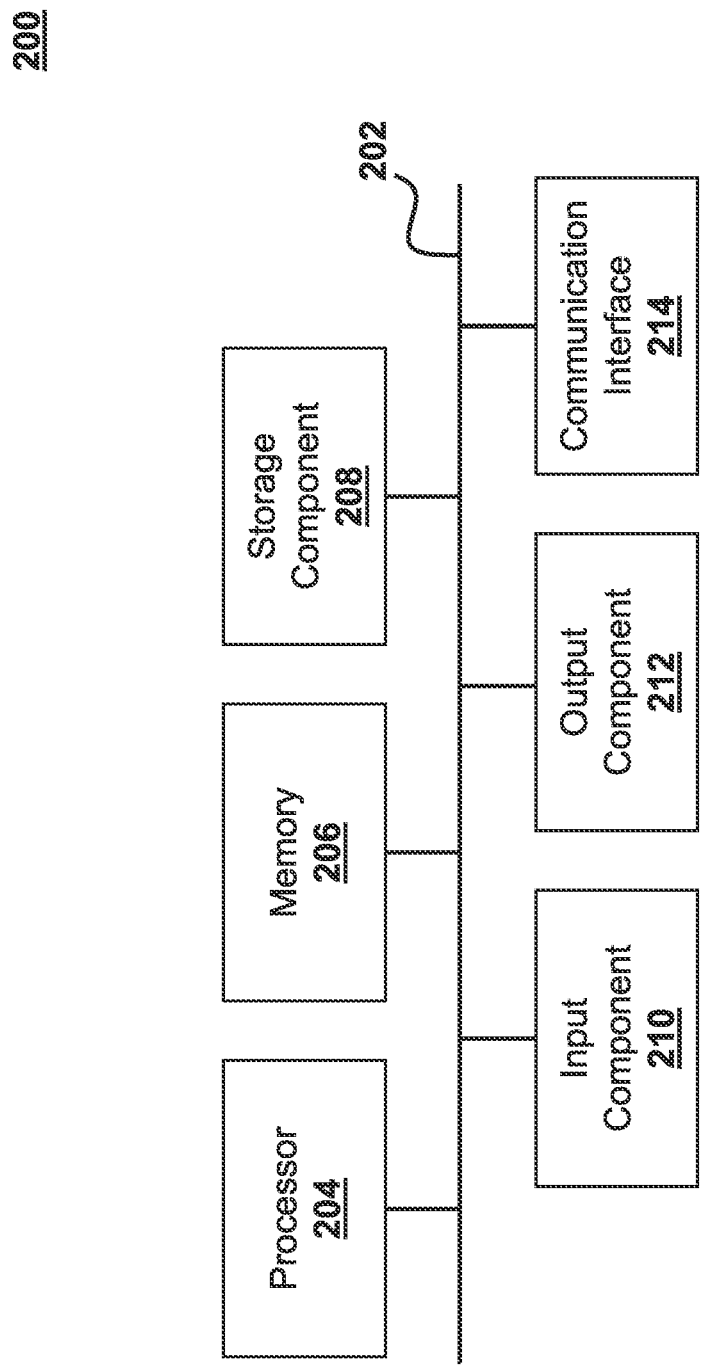
FIG. 2 is a diagram of a non-limiting embodiment of components of one or more devices shown in FIG. 1.

Referring now to FIG. 2, FIG. 2 is a diagram of example components of device 200. Device 200 may correspond to modulation device 102 and/or user device 104. In some non-limiting embodiments or aspects, modulation device 102 and/or user device 104 may include at least one device 200 and/or at least one component of device 200. As shown in FIG. 2, device 200 may include bus 202, processor 204, memory 206, storage component 208, input component 210, output component 212, and communication interface 214. Additionally or alternatively, device 200 may correspond to other devices disclosed herein, including power control module 404 and/or power source 406.

Bus 202 may include a component that permits communication among the components of device 200. In some non-limiting embodiments or aspects, processor 204 may be implemented in hardware, software, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read-only memory (ROM), and/or another type of dynamic or static storage device (e.g., flash memory, magnetic memory, optical memory, etc.) that stores information and/or instructions for use by processor 204. In some non-limiting embodiments, processor 204 may include a beam forming microprocessor as described herein.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touchscreen display, a keyboard, a keypad, a mouse, a button, a switch, a microphone, a camera, etc.). Additionally or alternatively, input component 210 may include a sensor for sensing information (e.g., a global positioning system (GPS) component, an accelerometer, a gyroscope, an actuator, etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmitter, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi® interface, a Bluetooth® interface, a Zigbee® interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally or alternatively, hardwired circuitry may be used in place of or in combination with software instructions to perform one or more processes described herein. Thus, embodiments or aspects described herein are not limited to any specific combination of hardware circuitry and software.

Memory 206 and/or storage component 208 may include data storage or one or more data structures (e.g., a database and/or the like). Device 200 may be capable of receiving information from, storing information in, communicating information to, or searching information stored in the data storage or one or more data structures in memory 206 and/or storage component 208. For example, the information may include input data, output data, transaction data, account data, or any combination thereof.

The number and arrangement of components shown in FIG. 2 are provided as an example. In some non-limiting embodiments or aspects, device 200 may include additional components, fewer components, different components, or differently arranged components than those shown in FIG. 2. Additionally or alternatively, a set of components (e.g., one or more components) of device 200 may perform one or more functions described as being performed by another set of components of device 200.

Figure 3:
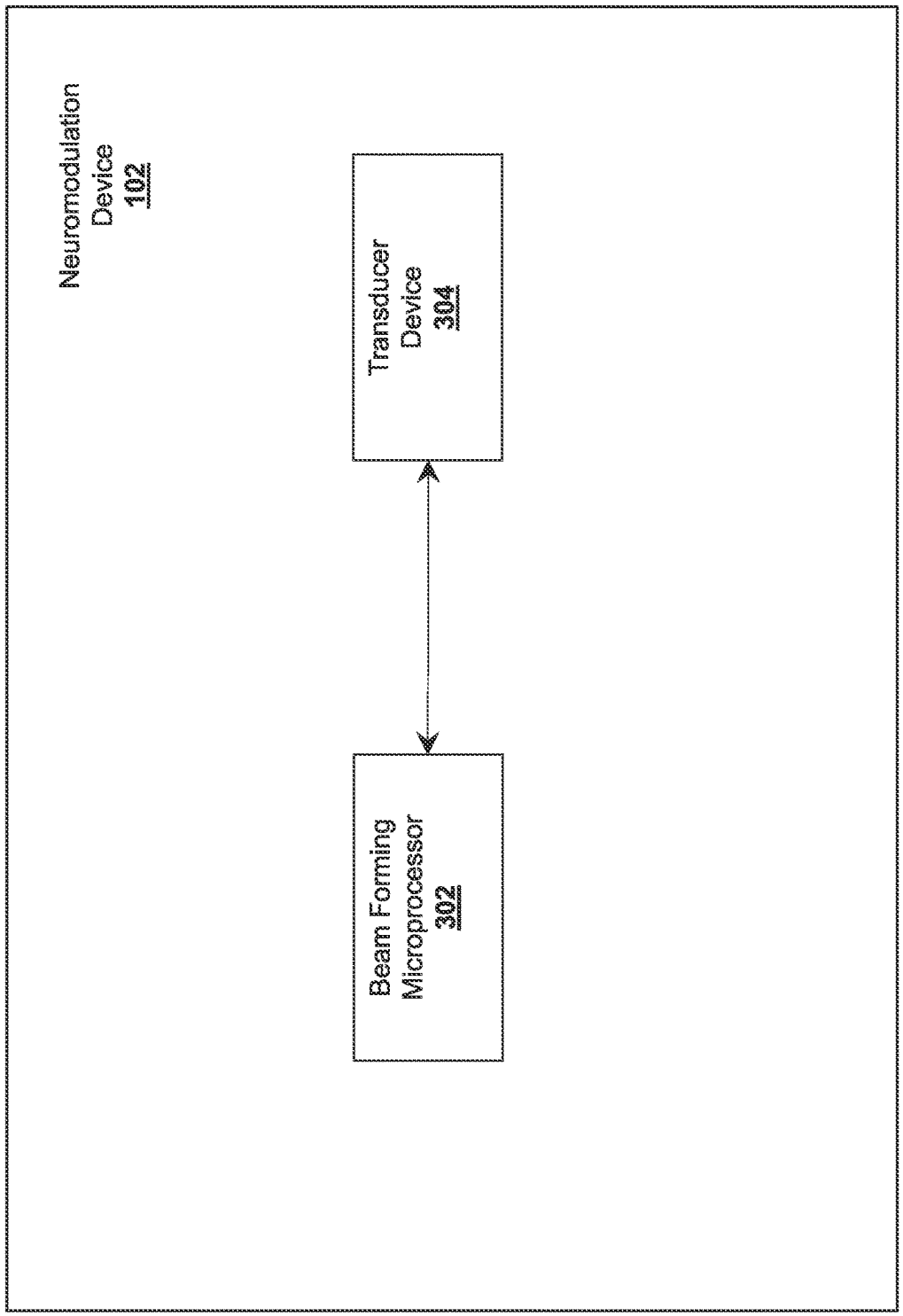
FIG. 3 is a diagram of a non-limiting embodiment of a modulation device.

Referring now to FIG. 3, FIG. 3 is a diagram of modulation device 102. As shown in FIG. 3, modulation device 102 may include beam forming microprocessor 302 and transducer device 304. In some non-limiting embodiments, beam forming microprocessor 302 and transducer device 304 may interconnect (e.g., establish a connection to communicate, establish a communication connection, etc.) via wired connections, wireless connections, or a combination of wired and wireless connections. In some non-limiting embodiments, beam forming microprocessor 302 and transducer device 304 may be connected via a bus (e.g., bus 202).

In some non-limiting embodiments, beam forming microprocessor 302 may include one or more devices that are configured to control transducer device 304. For example, beam forming microprocessor 302 may include a microprocessor that is configured to provide high-voltage, high-frequency electrical signals to transducer device 304 and transducer device 304 may convert the high-voltage, high-frequency electrical signals into an output, where the output may include an acoustic wave. In some non-limiting embodiments, beam forming microprocessor 302 may include a phase delay feature of that allows for steering and focusing of acoustic waves produced by transducer device 304.

In some non-limiting embodiments, beam forming microprocessor 302 may include the following specifications: a channel count from 1 to 32,768, electrical current limit per channel from 0.001 to 5 A, zero to peak voltage from 5 to 500V, peak-to-peak voltage from 10 to 1000V, and/or zero to peak negative from −5 to −500V. In some non-limiting embodiments, beam forming microprocessor 302 may include an application specific integrated circuit (ASIC). In some non-limiting embodiments, beam forming microprocessor 302 may have the following dimensions: a length in a range of 50-70 mm, a width in a range of 30-70 mm, and a height in a range of 1-20 mm. In some non-limiting embodiments, beam forming microprocessor 302 may include the following output specifications: voltage signal outputs in a range of 1 to 1,000V peak to peak, a clock frequency up to 500 MHz, and memory to store information, such as waveforms and algorithms (e.g., phasing algorithms for individual transducer device channel control to allow focusing and/or steering of an acoustic wave produced by the transducer device). In some non-limiting embodiments, beam forming microprocessor 302 may include the following input specifications: an interface (e.g., Bluetooth® interface) for receiving signals, on board programming, control of one or more channels, control of one or more channel delays, delay resolution in a range of 1 ns to 500 µs, and a plurality of input/output (I/O) pins for processing various information, including trigger conditions.

In some non-limiting embodiments, transducer device 304 may include one or more devices that are configured to produce an acoustic wave. For example, transducer device 304 may include a transducer that is configured to produce an acoustic wave (e.g., an ultrasonic beam, an ultrasonic wave, etc.) having specific parameters. In some non-limiting embodiments, transducer device 304 may include a transducer that can be used to send and receive signals (e.g., pulse-echo) and/or receive signals transmitted by an energy delivery transducer or another transducer (e.g., pitch-catch).

In some non-limiting embodiments, transducer device 304 may include an energy delivery transducer. For example, transducer device 304 may include an energy delivery transducer that is configured to provide an acoustic wave that may be configured to provide therapy to a patient, which may be used as a detection signal for steering a beam path of the acoustic wave, and/or the like. In some non-limiting embodiments, transducer device 304 may include a detection transducer (e.g., an imaging transducer). For example, transducer device 304 may include a detection transducer that is configured to receive an acoustic wave that is a reflection of an acoustic wave provided by transducer device 304 and provide data associated with the reflection of an acoustic wave. In some non-limiting embodiments, transducer device 304 may be configured to provide data associated with an image (e.g., an ultrasound image) of an object based on the reflection of an acoustic wave.

In some non-limiting embodiments, transducer device 304 may include a transducer array, where the transducer array include includes a plurality of transducer elements (e.g., individual transducer elements). In some non-limiting embodiments, the plurality of transducer elements may be connected with one or more ground plane electrodes on a first side and a signal channel connection on a second side (e.g., a side opposite the first side). In some non-limiting embodiments, the plurality of transducer elements may be controlled with signal channels individually (e.g., each transducer element controlled with one signal channel) or as a plurality (e.g., a set of transducer elements controlled with one signal channel). In one example, a first beam forming microprocessor (e.g., one beam forming microprocessor 302) may control a first set of transducer elements of a transducer array and a second beam forming microprocessor (e.g., one beam forming microprocessor 302) may control a first set of transducer elements of the transducer array.

In some non-limiting embodiments, transducer device 304 may be made (e.g., constructed, fabricated, etc.) from a material that may include lead zirconate titanate (PZT), polyvinylidene difluoride (PVDF), aluminum nitride (AlN), scandium (Sc) doped AlN, or a combination of these materials. In some non-limiting embodiments, transducer device 304 may include a gas matrix piezoelectric (GMP) array, a capacitive micro-machined acoustic transducer (cMUT) array and/or a piezoelectric micro-machined ultrasound transducer (pMUT) array. In some non-limiting embodiments, transducer device 304 may include a microelectronic mechanical systems (MEMS) transducer device.

In some non-limiting embodiments, transducer device 304 may be electrically connected to beam forming microprocessor 302 using a balls grid array (BGA), by being directly bonded via a flip chip, a through-silicon via (TSV), using a push/pull connector, using direct soldering, using wire-bond interconnects, and/or the like. In some non-limiting embodiments, transducer device 304 may be made (e.g., formed, constructed, fabricated, etc.) onto a flexible substrate, such as a flexible PCB and/or a flexible electrode, to allow for conformance of modulation device 302 to a body of a user.

Figure 4:
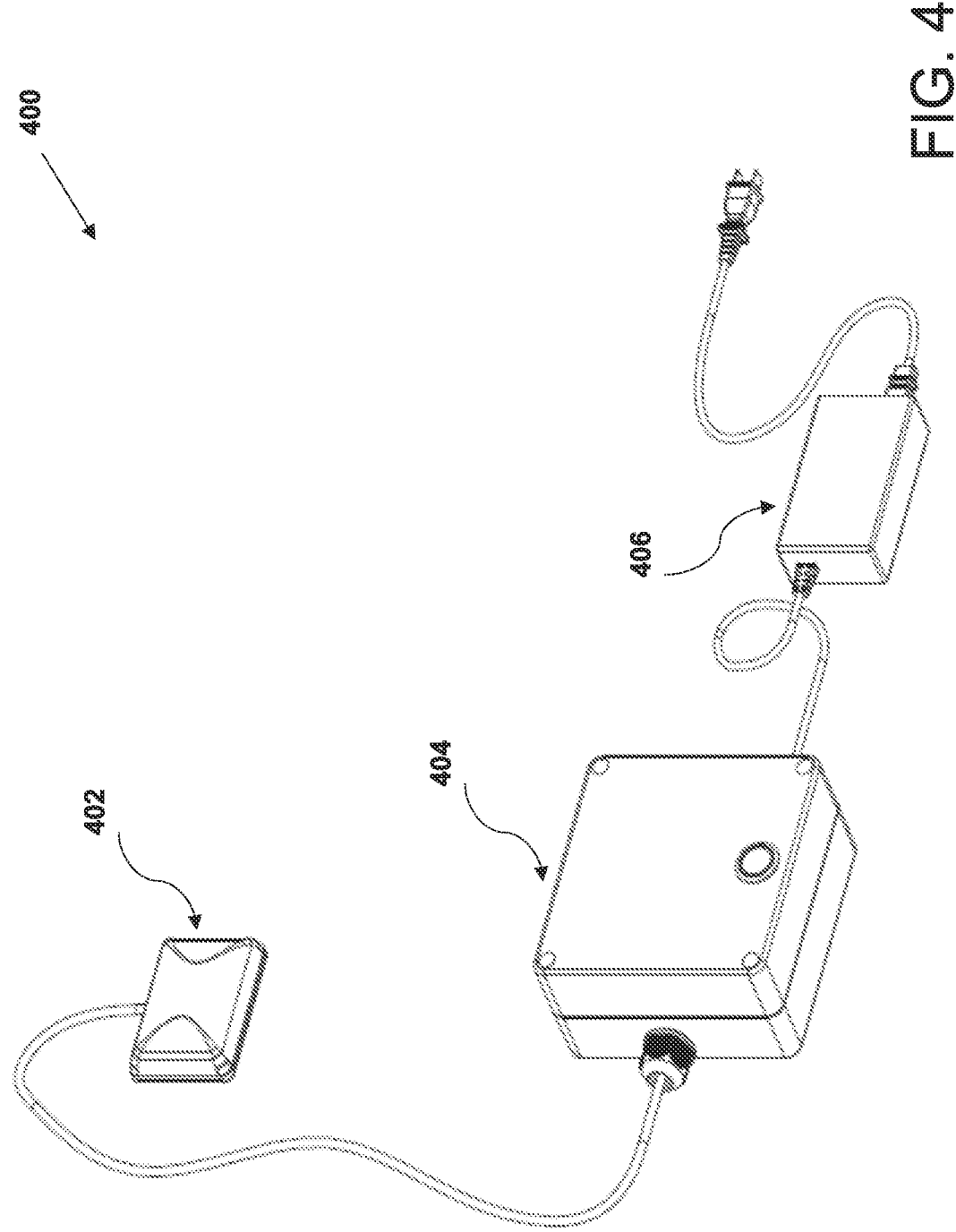
FIG. 4 is a diagram of a non-limiting embodiment of a system for modulation of a body of a user.

Referring now to FIG. 4, FIG. 4 is a diagram of system 400 for modulation of a body of a user (e.g., a patient, a recipient of treatment, etc.). As shown in FIG. 3, assembly 400 may include modulation device 402, power control module 404, and power source 406. In some non-limiting embodiments, power source 406 may include a device which receives and converts standard electrical power inputs. For example, power source 406 may include a power adapter which can accommodate standard electrical power inputs (e.g., a power signal in a range between 100-240V and having a frequency in a range between 50-60 Hz) and provide an amount of power in a range from 5 to 500 W. Power source 406 may include a plug that is configured to be plugged into a standard wall outlet. In some non-limiting embodiments, power source 406 may be configured to convert an AC power signal (e.g., an AC voltage) or to a DC power signal (e.g., a DC voltage). In some non-limiting embodiments, power control module 404 may include electronic circuitry that is configured to provide power conditioning for a power signal that is provided by modulation device 402.

Figure 5:
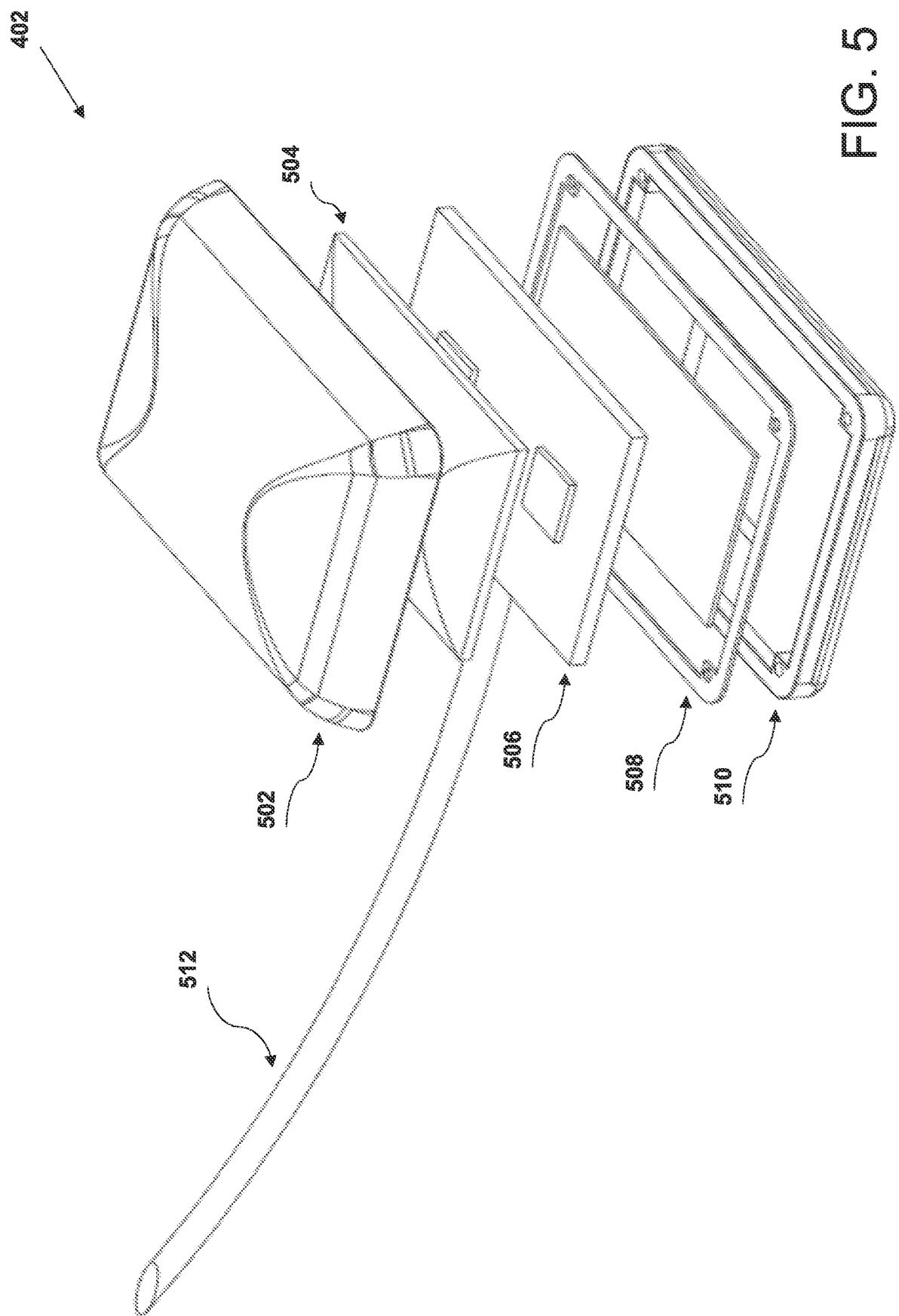
FIG. 5 is a diagram of a non-limiting embodiment of a modulation device.

Referring now to FIG. 5, FIG. 5 is a diagram of modulation device 402. As shown in FIG. 5, modulation device 402 may include upper housing section 502, heat dissipation device 504, pulser board assembly 506, support section 508, lower housing section 510, and cable 512.

In some non-limiting embodiments, upper housing section 502 and lower housing section 510 may be connected together to form a housing of modulation device 102. The housing may provide a seal (e.g., a liquid impervious seal, a hermetic seal, etc.) to components enclosed within the housing, including heat dissipation device 504, pulser board assembly 506, mask layer 508, and/or components thereof. In some non-limiting embodiments, the housing may include insulation, such as a heat resistant foam layer. The insulation may have a sufficient thickness to insulate the components within the housing from an external environment. In some non-limiting embodiments, upper housing section 502 and lower housing section 510 may be made (e.g., fabricated) separately. For example, upper housing section 502 may be made by an injection molding process from Acrylonitrile Butadiene Styrene (ABS) and lower housing section 510 may be injection molded with an acoustic matching material, such as ULTEM 2200 polyether imide and/or acrylic. In some non-limiting embodiments, the acoustic matching material of lower housing section 510 may be designed for use with acoustic waves in a range of 400-600 kHz and for use on skin with high structural integrity.

In some non-limiting embodiments, thermal management device 504 may include a device that is configured to dissipate heat generated by electrical components of pulser board assembly 506. As shown in FIG. 2, heat dissipation device 504 may include a heat sink. Additionally or alternatively, heat dissipation device 504 may include a fan.

In some non-limiting embodiments, mask layer 508 may include a layer of opaque material. For example, mask layer 508 may include a layer of opaque plastic, a layer of opaque rubber, and/or the like.

In some non-limiting embodiments, cable 512 may include electrical cables (e.g., conductors, wires, etc.) that provide a communication connection (e.g., a connection for communicating data signals) and/or a power connection (e.g., a connection for power signals) between modulation device 402 and power control module 404.

Figure 6:
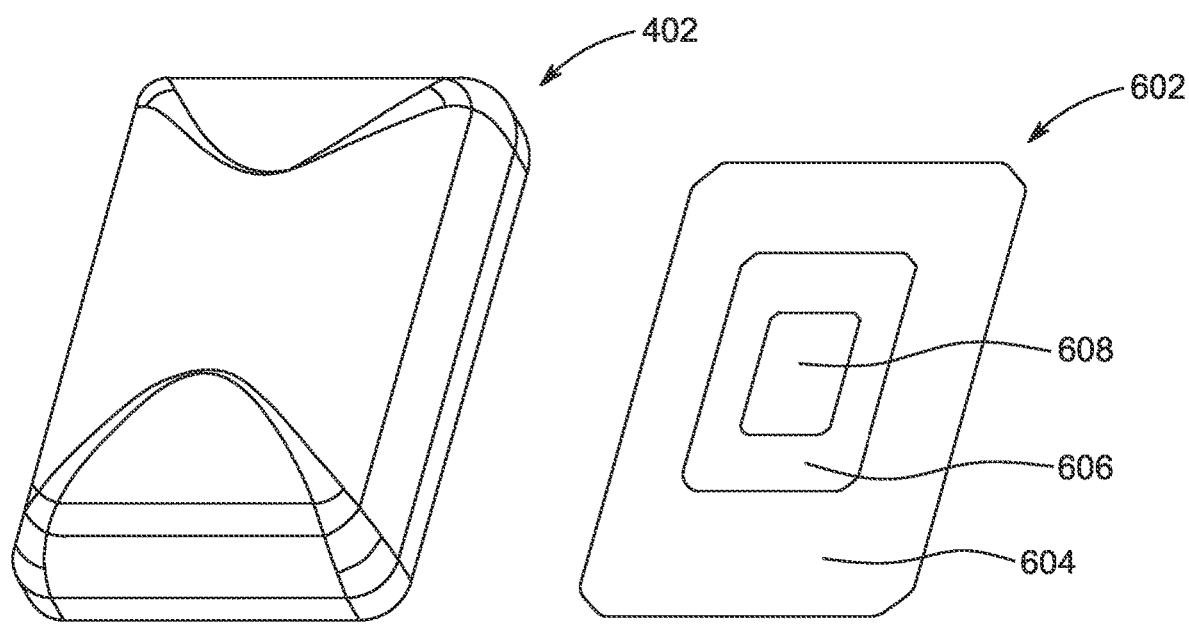
FIG. 6 is a diagram of a non-limiting embodiment of an adhesive pad to be used with the phased array modulation device shown in FIG. 5.

Referring now to FIG. 6, FIG. 6 is a diagram of modulation device 402 and coupling pad 502. In some non-limiting embodiments, coupling pad 502 may include an adhesive for coupling modulation device 402 to skin of a user. For example, coupling pad 502 may include a biocompatible adhesive. In some non-limiting embodiments, coupling pad 502 may include a material for coupling modulation device 402 to a body of a user. For example, coupling pad 502 may include a solid coupling material or semi-solid coupling material. The semi-solid coupling material may include a hydrogel having an internal water content that is greater than 20%. In some non-limiting embodiments, the material for coupling may include an adhesive, a liquid-based acoustic coupling gel, and/or the like. In some non-limiting embodiments, coupling pad 502 may be disposable. As shown in FIG. 3, coupling pad 502 may include outer portion 604 and central portion 606. Central portion 606 may include aperture 608. In some non-limiting embodiments, central portion 606 may include a hydrogel material that provides acoustic coupling of modulation device 402 to acoustically match modulation device 402 to the skin of the user during operation. In some non-limiting embodiments, outer portion 604 (e.g., a perimeter of outer portion 604) may include a medical adhesive that holds modulation device 402 in place on the body of the user.

Figure 7:
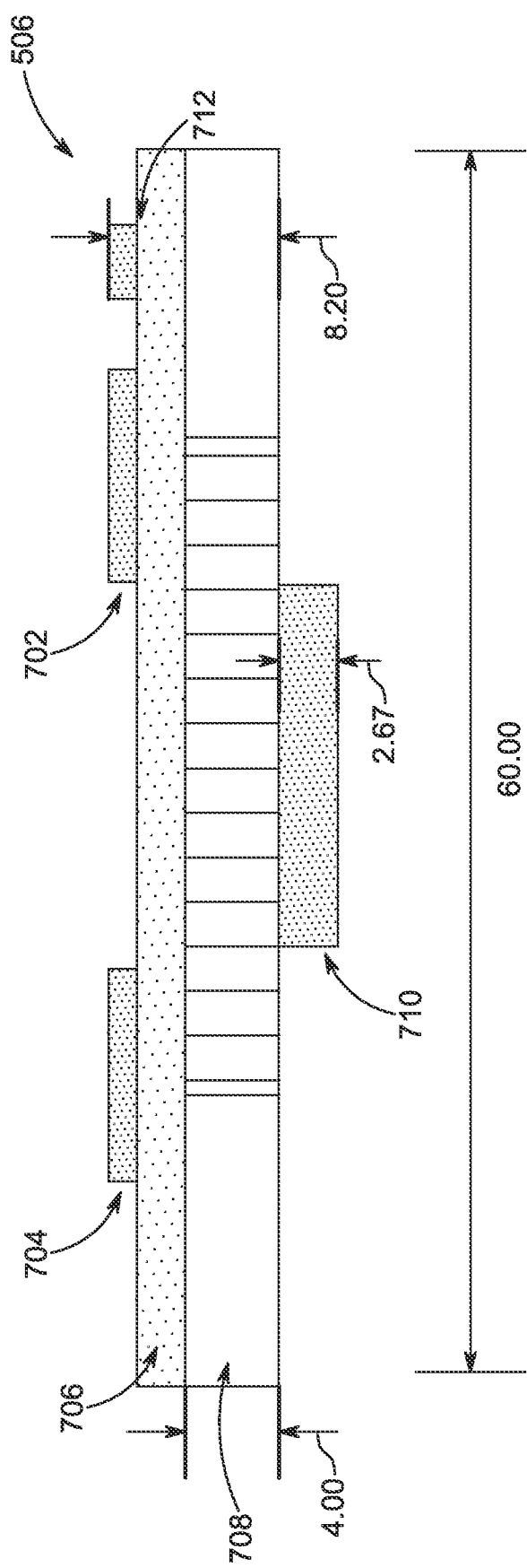
FIG. 7 is a diagram of a non-limiting embodiment of a pulser board assembly of the modulation device shown in FIG. 5.

Referring now to FIG. 7, FIG. 7 is a diagram of pulser board assembly 506. As shown in FIG. 7, pulser board assembly 506 may include first beam forming microprocessor 702, second beam forming microprocessor 704, PCB 706, connector 708, transducer assembly 710, and one more auxiliary electrical components 712. In some non-limiting embodiments, pulser board assembly 506 may have the following dimensions: a length in a range of 10-250 mm, a width in a range of 10-250 mm, and a height in a range of 1-50 mm. In one example, pulser board assembly 506 has a height in a range of 1 mm to 100 mm, a width in a range of 10 mm to 500 mm, and a length in a range of 10 mm to 500 mm. In some non-limiting embodiments, first beam forming microprocessor 702 and second beam forming microprocessor 704 are connected to PCB 706 and PCB 706 is positioned on connector 708. In some non-limiting embodiments, first beam forming microprocessor 702 and second beam forming microprocessor 704 are connected to PCB 706 and PCB 706 is connected to transducer assembly 710 such that connector 708 is not present. In some non-limiting embodiments, first beam forming microprocessor 702 and second beam forming microprocessor 704 are connected to a connector structure (e.g., a substrate, a flip chip, a through-silicon via (TSV), a wire bond, etc.) that is connected to transducer assembly 710.

In some non-limiting embodiments, first beam forming microprocessor 702 and/or second beam forming microprocessor 704 may be the same or similar to beam forming microprocessor 302. In some non-limiting embodiments, first beam forming microprocessor 702 and/or second beam forming microprocessor 704 are positioned on a top surface of PCB 706. In some non-limiting embodiments, first beam forming microprocessor 702 may include a system on chip (SoC) with capabilities, but not limited, to execute algorithms and data analytics. Additionally or alternatively, second beam forming microprocessor 704 may include a programmable beam former with capabilities to drive one or more channels (e.g., data channels). In some non-limiting embodiments, second beam forming microprocessor 704 may be configured to control transducer assembly 710 using individual channel control for phasing and/or focusing an acoustic wave provided by transducer assembly 710 with +90V to −90V control signals (e.g., excitation signals) provided to transducer assembly 710.

In some non-limiting embodiments, first beam forming microprocessor 702 may be programmed to control transducer assembly 710 so that transducer assembly 710 produces specific acoustic waves (e.g., specific pulse sequences). The acoustic wave produced may include pulse sequences produced by transducer assembly 710 that control transducer assembly 710 (e.g., that drive the independent transducer elements of transducer assembly 710). In some non-limiting embodiments, transducer assembly 710 may provide feedback (e.g., electrical pulse feedback regarding an acoustic wave) to second beam forming microprocessor 704. In some non-limiting embodiments, transducer assembly 710 may condition the feedback before transmitting the feedback to other components (e.g., first beam forming microprocessor 702) of pulser board assembly 506.

In some non-limiting embodiments, connector 708 is configured to provide an electrical connection between second beam forming microprocessor 704 and transducer assembly 710. In some non-limiting embodiments, connector 708 may include a structure that connects first beam forming microprocessor 702/second beam forming microprocessor 704 and transducer assembly 710. For example, connector 708 may include a balls grid array (BGA), a bond via a flip chip through a silicon via, a push/pull connector, a direct soldering element, a wire-bond interconnect, and/or the like.

In some non-limiting embodiments, transducer assembly 710 may be the same or similar to transducer device 304. In some non-limiting embodiments, transducer assembly 710 may include one or more transducer devices 304. In some non-limiting embodiments, transducer assembly 710 may be positioned on (e.g., positioned on a bottom surface of) connector 708. In some non-limiting embodiments, pulser board assembly 506 may have the following dimensions: a height of 2.67 mm.

In some non-limiting embodiments, auxiliary electrical component 712 may include a capacitor. For example, auxiliary electrical component 712 may include a capacitor that is used for charging and discharging a voltage when the voltage of a power signal provided to second beam forming microprocessor 704 transitions from one state (e.g., a high voltage state) to another state (e.g., a low voltage state).

Figure 8A:
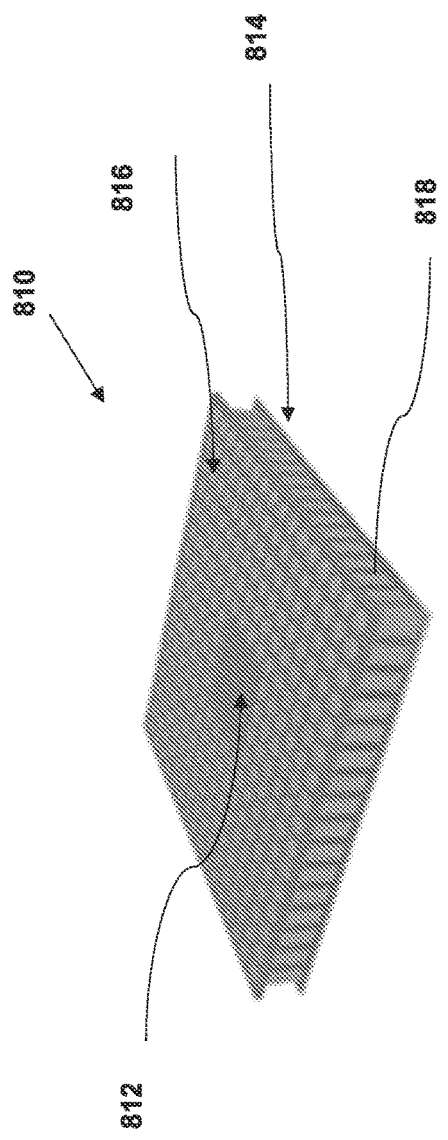
FIGS. 8A and 8B are diagrams of a non-limiting embodiment of a transducer assembly.
Figure 8B:
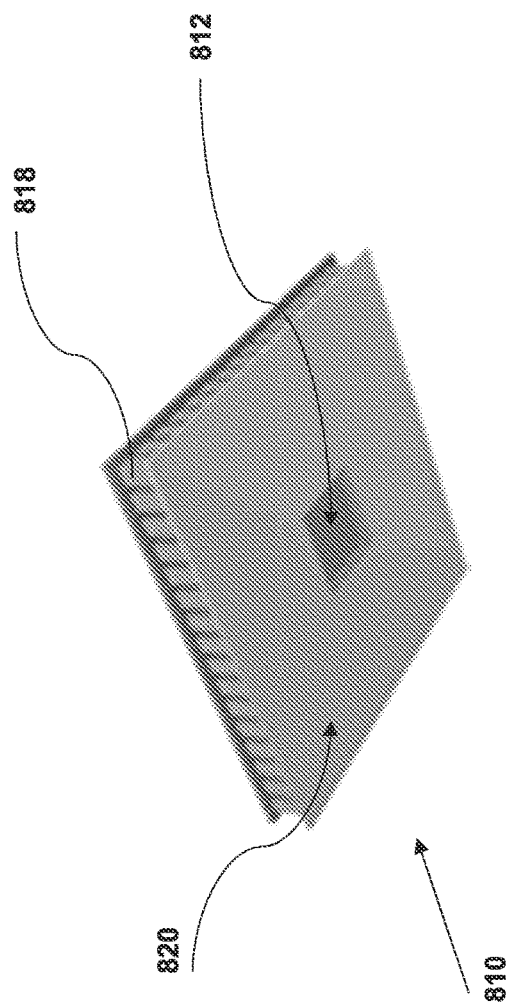

Referring now to FIGS. 8A and 8B, FIGS. 8A and 8B are diagrams of transducer assembly 810. As shown in FIGS. 8A and 8B, transducer assembly 810 may include detection transducer device 812 and energy delivery transducer device 814. As further shown in FIG. 8A, detection transducer device 812 may be coupled to energy delivery transducer device 814 via PCB 816. As further shown in FIG. 8B, detection transducer device 812 may be coupled to energy delivery transducer device 814 via PCB 820. As further shown in FIGS. 8A and 8B, energy delivery transducer device 814 may include transducer elements 818. In some non-limiting embodiments, transducer elements 818 may include rods made from lead zirconate titanate (PZT). In some non-limiting embodiments, detection transducer device 812 and/or energy delivery transducer device 814 may be the same or similar to transducer device 304. In some non-limiting embodiments, transducer assembly 810 may be the same or similar to transducer assembly 710.

Figure 9:
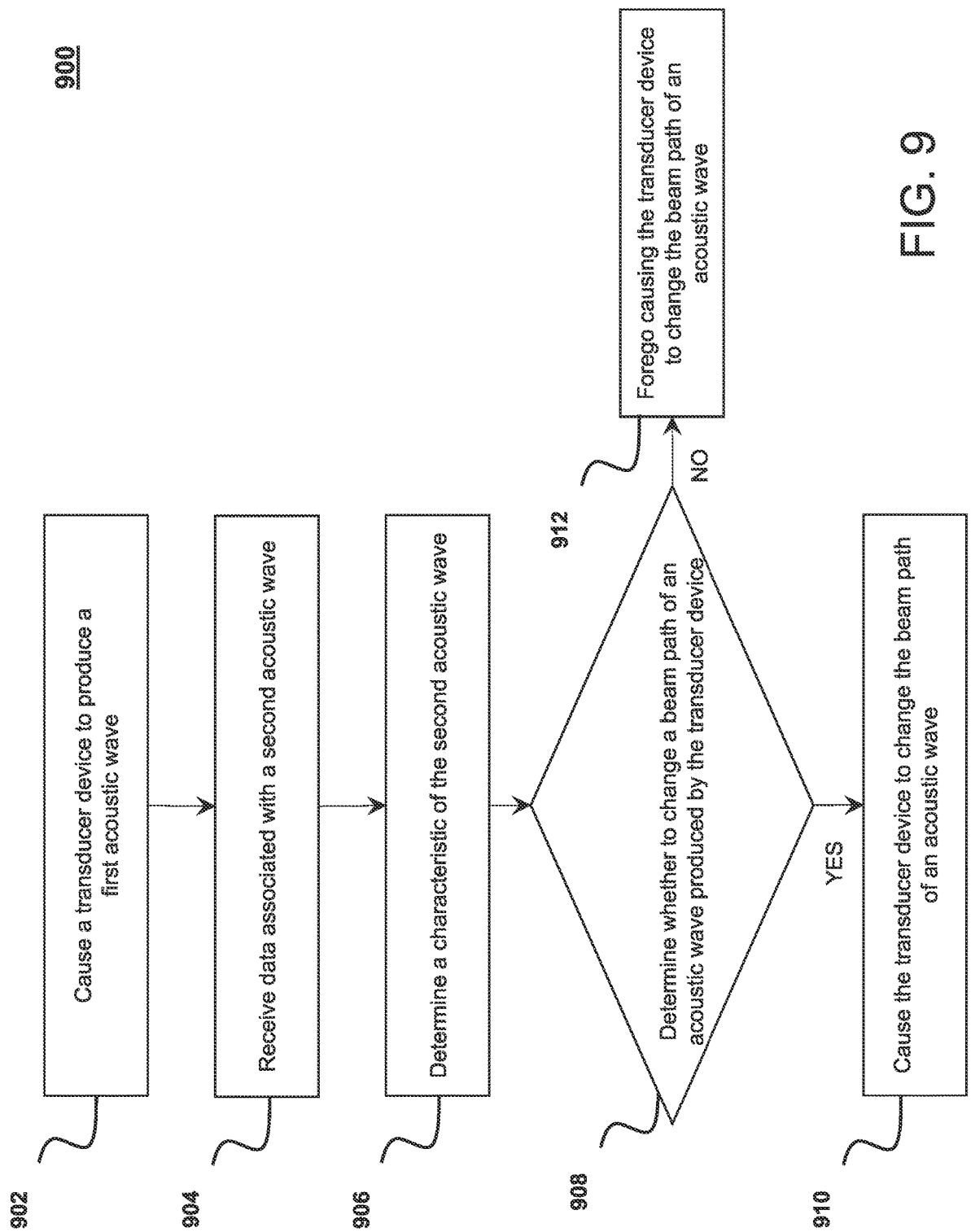
FIG. 9 is a flowchart of a non-limiting embodiment of a process for providing an acoustic wave to a target location.

Referring now to FIG. 9, FIG. 9 is a flowchart of a non-limiting aspect or embodiment of a process 900 for providing an acoustic wave to a target location. In some non-limiting embodiments or aspects, one or more of the functions (e.g., operations, actions, etc.) described with respect to process 900 may be performed (e.g., completely, partially, etc.) by modulation device 102. In some non-limiting embodiments or aspects, one or more of the steps of process 900 may be performed (e.g., completely, partially, and/or the like) by another device or a group of devices separate from and/or including modulation device 102, such as user device 104. In some non-limiting embodiments, one or more of the functions described with respect to process 900 may be performed by components of modulation device 102. For example, one or more of the functions described with respect to process 900 may be performed by beam forming microprocessor 302 and/or transducer device 304. In some non-limiting embodiments, while one or more of the functions described with respect to process 900 are described as being performed by modulation device 102 and/or components of modulation device 102, other devices and/or components of other devices described herein may perform one or more of the functions described with respect to process 900. For example, modulation device 402, first beam forming microprocessor 702, second beam forming microprocessor 704, transducer assembly 710, and/or transducer assembly 810 may perform one or more of the functions described with respect to process 900 despite that only modulation device 102 and/or components of modulation device 102 are described as performing the one or more functions.

As shown in FIG. 9, at step 902, process 900 may include causing a transducer device to produce a first acoustic wave. For example, modulation device 102 may cause transducer device 304 (e.g., an energy delivery transducer of transducer device 304) to produce the first acoustic wave. In some non-limiting embodiments, the first acoustic wave may include a plurality of pulses having a pulse repetition frequency. In some non-limiting embodiments, a pulse width of each pulse of the plurality of pulses is in a range of 10 ns to 10 µs. Additionally, or alternatively, the pulse repetition frequency is in a range of 1 Hz to 50 Hz. In some non-limiting embodiments, the first acoustic wave may have a bandwidth of 20% to 150% of peak frequency, wherein the peak frequency is a range of 50 kHz to 5 MHz. In some non-limiting embodiments, a number of cycles per pulse width of a pulse of the first acoustic wave is in a range of 1 to 5.

In some non-limiting embodiments, the first acoustic wave may include an acoustic wave that is to be detected by a detection transducer to allow for changing (e.g., steering, adjusting, etc.) a beam path of an acoustic wave produced by transducer device 304. In some non-limiting embodiments, modulation device 102 may cause an energy delivery transducer of transducer device 304 to produce the first acoustic wave as a detection signal. For example, beam forming microprocessor 302 of modulation device 102 may transmit a control signal to an energy delivery transducer of transducer device 304. The energy delivery transducer of transducer device 304 may produce the first acoustic wave as the detection signal so that a detection transducer of transducer device 304 may receive a second acoustic wave that is a reflection of the first acoustic wave.

As shown in FIG. 9, at step 904, process 900 may include receiving data associated with a second acoustic wave. For example, modulation device 102 (e.g., beam forming microprocessor 302 of modulation device 102) may receive data associated with the second acoustic wave, which is an acoustic wave that is a reflection of the first acoustic wave. In some non-limiting embodiments, a detection transducer of transducer device 304 may receive the second acoustic wave, which is a reflection of the first acoustic wave, and detection transducer of transducer device 304 may transmit the data associated with the second acoustic wave to beam forming microprocessor 302 of modulation device 102. In some non-limiting embodiments, the data associated with the second acoustic wave may include data associated with a phase of the second acoustic wave and/or data associated with an amplitude of the second acoustic wave. In some non-limiting embodiments, the data associated with the second acoustic wave may include data associated with a time at which the second acoustic wave was received by transducer device 304 (e.g., by a detection transducer of transducer device 304).

As shown in FIG. 9, at step 906, process 900 may include determining a characteristic of the second acoustic wave. For example, modulation device 102 (e.g., beam forming microprocessor 302 of modulation device 102) may determine the characteristic of the second acoustic wave. In some non-limiting embodiments, the characteristic of the second acoustic wave may include a phase delay between the first acoustic wave and the second acoustic wave. Additionally or alternatively, the characteristic of the second acoustic wave may include an amplitude of the second acoustic wave. In some non-limiting embodiments, the phase delay may include a difference in time between the first acoustic wave and the second acoustic wave. For example, the phase delay may include the difference in time between a time at which the first acoustic wave was transmitted (e.g., transmitted by transducer device 304) and a time at which the second acoustic wave was received (e.g., received by transducer device 304).

In some non-limiting embodiments, modulation device 102 may perform an action based on the second acoustic wave. For example, modulation device 102 may generate an image based on the second acoustic wave (e.g., the characteristic of the second acoustic wave). In another example, modulation device 102 may provide an indication based on the second acoustic wave (e.g., the characteristic of the second acoustic wave). In some non-limiting embodiments, the indication may include an indication associated with discontinuing a treatment, an indication associated with improper placement of modulation device 102 (e.g., of transducer device 304 of modulation device 102), an indication associated with a prompt for receiving a user input, or any combination thereof.

In some non-limiting embodiments, modulation device 102 may determine the phase delay between the first acoustic wave and the second acoustic wave and determine an amplitude of the second acoustic wave. In some non-limiting embodiments, modulation device 102 may determine whether the amplitude of the second acoustic wave satisfies a threshold (e.g., an amplitude threshold, a threshold value of amplitude of an acoustic wave, a predetermined threshold value of amplitude of an acoustic wave, etc.). In some non-limiting embodiments, modulation device 102 may determine whether the phase delay between the first acoustic wave and the second acoustic wave satisfies a threshold (e.g., a phase delay threshold, a threshold value of phase delay of acoustic waves, a predetermined threshold value of phase delay of acoustic waves, etc.). In some non-limiting embodiments, modulation device 102 may perform an action based on determining whether the amplitude of the second acoustic wave satisfies a threshold and/or determining whether the phase delay between the first acoustic wave and the second acoustic wave satisfies a threshold. For example, modulation device 102 may perform the action based on determining that the amplitude of the second acoustic wave satisfies the threshold and/or determining that the phase delay between the first acoustic wave and the second acoustic wave satisfies the threshold.

As shown in FIG. 9, at step 908, process 900 may include determining whether to change a beam path of an acoustic wave produced by the transducer device. For example, modulation device 102 (e.g., beam forming microprocessor 302 of modulation device 102) may determine whether to change a beam path of an acoustic wave produced by transducer device 304. In some non-limiting embodiments, modulation device 102 may determine whether to change the beam path of an acoustic wave produced by the transducer device based on the characteristic of the second acoustic wave. For example, modulation device 102 may determine whether to change the beam path of an acoustic wave produced by the transducer device based on determining whether the amplitude of the second acoustic wave satisfies a threshold, the phase delay between the first acoustic wave and the second acoustic wave, and/or determining whether the phase delay between the first acoustic wave and the second acoustic wave satisfies a threshold.

In some non-limiting embodiments, if modulation device 102 determines that the amplitude of the second acoustic wave satisfies a threshold and/or determines that the phase delay between the first acoustic wave and the second acoustic wave satisfies a threshold, then modulation device 102 may determine to change the beam path of an acoustic wave produced by transducer device 304. Additionally or alternatively, if modulation device 102 determines that the amplitude of the second acoustic wave does not satisfy a threshold and/or determines that the phase delay between the first acoustic wave and the second acoustic wave does not satisfy a threshold, then modulation device 102 may determine not to change the beam path of an acoustic wave produced by transducer device 304.

As shown in FIG. 9, at step 910 ("YES"), process 900 may include causing the transducer device to change the beam path of an acoustic wave. For example, modulation device 102 (e.g., beam forming microprocessor 302 of modulation device 102) may cause transducer device 304 to change the beam path of an acoustic wave provided by transducer device 304 based on determining to change the beam path of an acoustic wave produced by transducer device 304. In some non-limiting embodiments, modulation device 102 may determine an amount of change to be made to the beam path of an acoustic wave produced by transducer device 304 from the beam path of the first acoustic wave based on determining to change the beam path of an acoustic wave produced by transducer device 304.

In some non-limiting embodiments, modulation device 102 may determine a change (e.g., an amount of change) in the beam path of an acoustic wave produced by the transducer device from the beam path of the first acoustic wave based on the phase delay and determining whether the amplitude of the second acoustic wave satisfies a threshold. In some non-limiting embodiments, modulation device 102 may determine an amount of change to be made to the beam path of an acoustic wave produced by transducer device 304 from the beam path of the first acoustic wave based on the characteristic of the second acoustic wave. For example, modulation device 102 may determine an amount of change to be made to the beam path of an acoustic wave produced by transducer device 304 from the beam path of the first acoustic wave based on determining whether the amplitude of the second acoustic wave satisfies a threshold and/or determining whether the phase delay between the first acoustic wave and the second acoustic wave satisfies a threshold.

In some non-limiting embodiments, modulation device 102 may cause transducer device 304 to change the beam path of an acoustic wave produced by transducer device 304 based on an amount of change to be made to the beam path of an acoustic wave produced by the transducer device from the beam path of the first acoustic wave. For example, beam forming microprocessor 302 of modulation device 102 may transmit a control signal to an energy delivery transducer of transducer device 304 and the energy delivery transducer of transducer device 304 may change the beam path based on the amount of change to be made to the beam path.

As shown in FIG. 9, at step 912 ("NO"), process 900 may include foregoing causing the transducer device to change the beam path of an acoustic wave. For example, modulation device 102 (e.g., beam forming microprocessor 302 of modulation device 102) may forego causing transducer device 304 to change the beam path of an acoustic wave provided by transducer device 304 based on determining not to change the beam path of an acoustic wave produced by transducer device 304. In some non-limiting embodiments, modulation device 102 may determine that no amount of change is to be made to the beam path of an acoustic wave produced by transducer device 304 from the beam path of the first acoustic wave based on determining not to change the beam path of an acoustic wave produced by transducer device 304.

In some non-limiting embodiments, modulation device 102 may determine that no amount of change is to be made to the beam path of an acoustic wave produced by transducer device 304 from the beam path of the first acoustic wave based on the characteristic of the second acoustic wave. For example, modulation device 102 may determine that no amount of change is to be made to the beam path of an acoustic wave produced by transducer device 304 from the beam path of the first acoustic wave based on determining whether the amplitude of the second acoustic wave satisfies a threshold and/or determining whether the phase delay between the first acoustic wave and the second acoustic wave satisfies a threshold.

In some non-limiting embodiments, modulation device 102 may cause transducer device 304 to produce a third acoustic wave. For example, modulation device 102 may cause transducer device 304 to produce a third acoustic wave along the beam path based on causing transducer device 304 to change the beam path of an acoustic wave produced by transducer device 304 from the beam path of the first acoustic wave. In another example, modulation device 102 may cause transducer device 304 to produce a third acoustic wave along the beam path of the first acoustic wave. In some non-limiting embodiments, the third acoustic wave may include a plurality of pulses having a pulse repetition frequency. In some non-limiting embodiments, each pulse of the plurality of pulses has a pulse width in a range of 1 μs to 500 ms. In one example, each pulse of the plurality of pulses has a pulse width in a range of 10 μs to 200 ms. Additionally or alternatively, the pulse repetition frequency may be in a range of 25 Hz to 1000 Hz. In some non-limiting embodiments, the third acoustic wave may have a bandwidth of 1-70% of peak frequency, and the peak frequency may be in a range of 50 kHz to 5 MHz. In some non-limiting embodiments, a number of cycles per pulse width of a pulse of the third acoustic wave may be in a range of 5 to 2,500,000. In one example, a number of cycles per pulse width of a pulse of the third acoustic wave may be in a range of 5 to 500.

In some non-limiting embodiments, modulation device 102 may cause an energy delivery transducer of transducer device 304 to produce the third acoustic wave as a treatment signal. For example, beam forming microprocessor 302 of modulation device 102 may transmit a control signal to an energy delivery transducer of transducer device 304. The energy delivery transducer of transducer device 304 may produce the third acoustic wave as the treatment signal so that a target location of a body of a user receives the third acoustic wave as a treatment.

Referring now to FIGS. 10A-10D, FIGS. 10A-10D are diagrams of a non-limiting embodiment of an example implementation 1000 of a process (e.g., process 900) for providing an acoustic wave to a target location. As shown in FIGS. 10A-10D, implementation 1000 may include modulation device 102. In some non-limiting embodiments, one or more of the functions described with respect to implementation 1000 may be performed (e.g., completely, partially, etc.) by modulation device 102. In some non-limiting embodiments or aspects, one or more of the steps of implementation 1000 may be performed (e.g., completely, partially, and/or the like) by another device or a group of devices separate from and/or including modulation device 102, such as user device 104. In some non-limiting embodiments, one or more of the functions described with respect to implementation 1000 may be performed by components of modulation device 102. For example, one or more of the functions described with respect to implementation 1000 may be performed by beam forming microprocessor 302 and/or transducer device 304. In some non-limiting embodiments, while one or more of the functions described with respect to implementation 1000 are described as being performed by modulation device 102 and/or components of modulation device 102, other devices and/or components of other devices described herein may perform one or more of the functions described with respect to implementation 1000. For example, modulation device 402, first beam forming microprocessor 702, second beam forming microprocessor 704, transducer assembly 710, and/or transducer assembly 810 may perform one or more of the functions described with respect to process 900 despite that only modulation device 102 and/or components of modulation device 102 are described as performing the one or more functions.

Figure 10A:
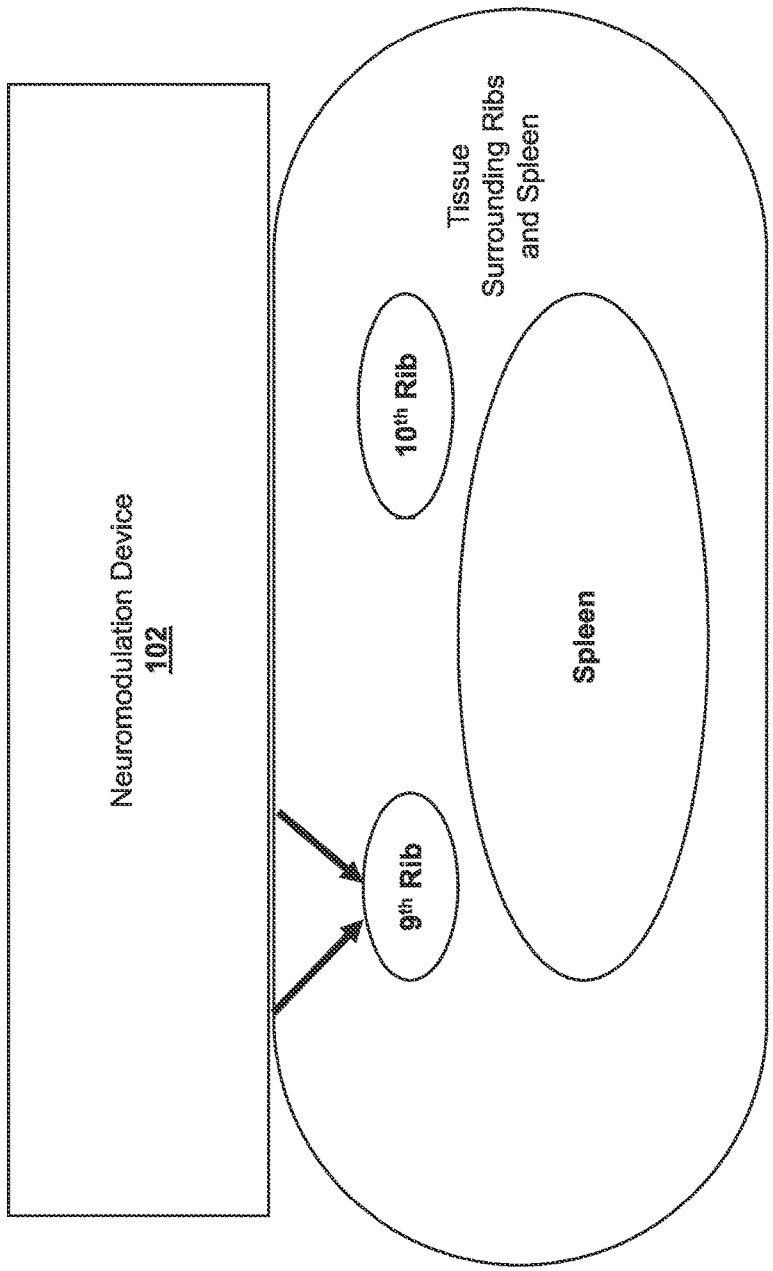
Figure 10B:
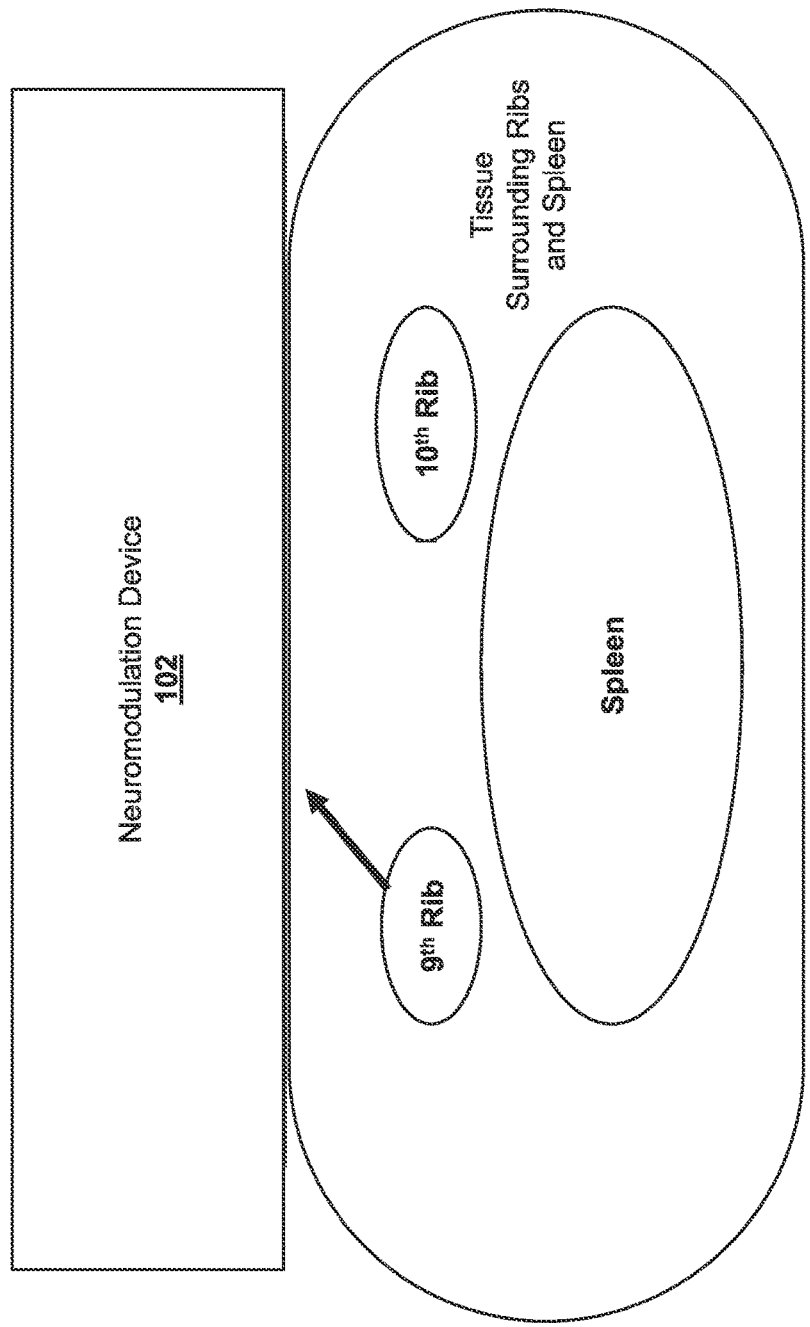

As shown by reference number 1010 in FIG. 10A, modulation device 102 may produce a first acoustic wave. In some non-limiting embodiments, modulation device 102 may cause a first transducer device (e.g., an energy delivery transducer of transducer device 304) to produce a first acoustic wave. As shown by reference number 1020 in FIG. 10B, modulation device 102 may receive data associated with a second acoustic wave. In some non-limiting embodiments, a beam forming microprocessor (e.g., beam forming microprocessor 302 of modulation device 102) of modulation device 102 may receive data associated with the second acoustic wave, which is an acoustic wave that is a reflection of the first acoustic wave off of the ninth rib of a body of a user. In some non-limiting embodiments, a second transducer device (e.g., a detection transducer of transducer device 304) of modulation device 102 may receive the second acoustic wave and the second transducer device may transmit the data associated with the second acoustic wave to the beam forming microprocessor.

As shown by reference number 1030 in FIG. 10C, modulation device 102 may determine a characteristic of the second acoustic wave. In some non-limiting embodiments, the characteristic of the second acoustic wave may include a phase delay between the first acoustic wave and the second acoustic wave. Additionally or alternatively, the characteristic of the second acoustic wave may include an amplitude of the second acoustic wave. In some non-limiting embodiments, the phase delay may include a difference in time between the first acoustic wave and the second acoustic wave. For example, the phase delay may include the difference in time between a time at which the first acoustic wave was transmitted by the first transducer device and a time at which the second acoustic wave was received by the second transducer device.

Figure 10D:
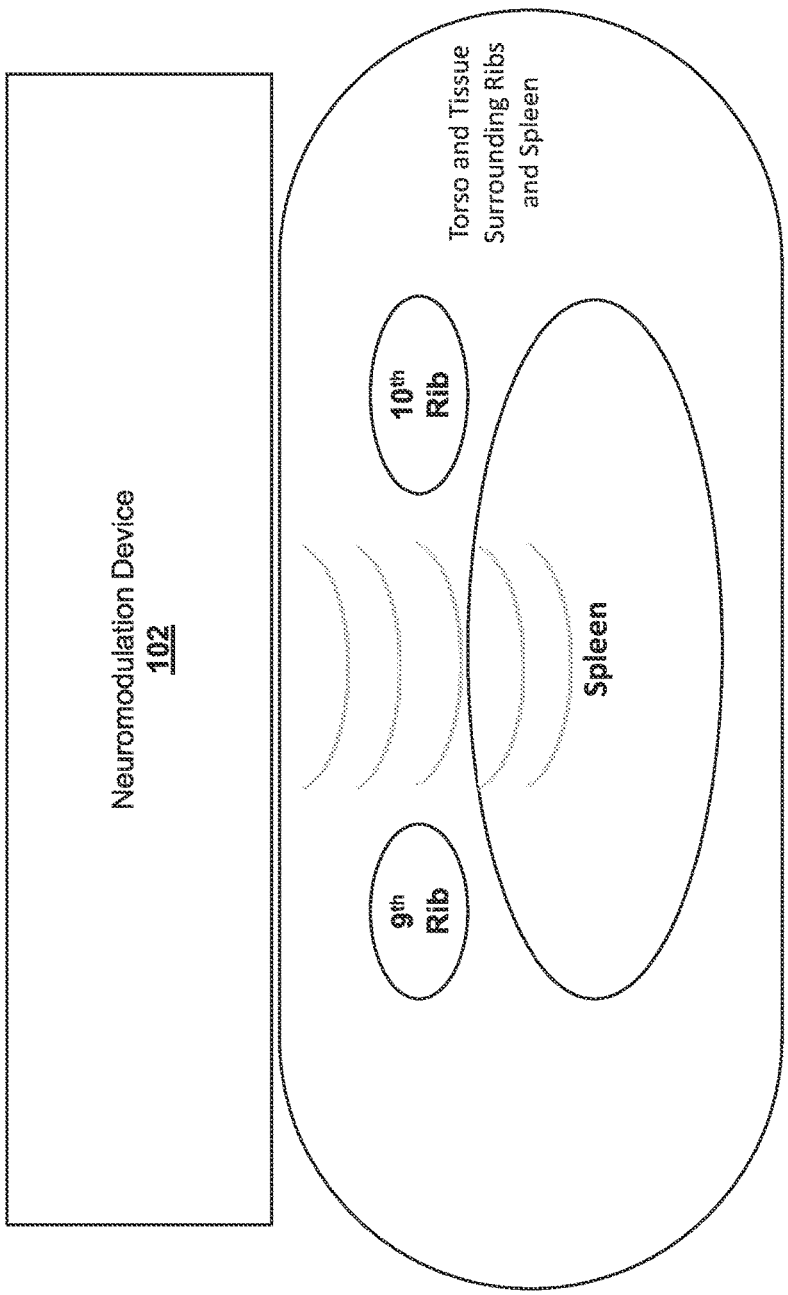

As shown by reference number 1040 in FIG. 10D, modulation device 102 may determine to change the beam path of an acoustic wave. In some non-limiting embodiments, the beam forming microprocessor of modulation device 102 may determine to change the beam path of an acoustic wave produced by the first transducer device from the beam path of the first acoustic wave based on the characteristic of the second acoustic wave. In some non-limiting embodiments, modulation device 102 may cause the first transducer device to change the beam path of an acoustic wave provided by the first transducer device based on determining to change the beam path of an acoustic wave. As further shown by reference number 1050 in FIG. 10D, modulation device 102 may produce a third acoustic wave. In some non-limiting embodiments, modulation device 102 may cause the first transducer device to produce the third acoustic wave to a target location of the spleen of the user.

Also provided herein are methods of using acoustic waves generated by a transducer device (e.g., an ultrasonic transducer device), for example, a device as described herein, to modulate a patient's immune system. As used herein, the term "patient" is any animal, including humans, and a "human patient" is any human. As used herein, the term "modulate" means modify the function of, for example, by increasing or decreasing release of one or more factors, such as cytokines, other immune factors, growth factors, and/or other peptides and/or proteins. Non-limiting examples of factors whose levels can be increased or decreased using a device as described herein include c-c motif chemokine ligand 2 (CCL2, also called MCP-1 or JE), c-x-c motif chemokine ligand 1 (CXCL1, also called KC, MGSA-α, or Gro-α), c-x-c motif chemokine ligand 2 (CXCL2, also called Gro-β or MIP-2), interleukin-1 alpha (IL-1α and beta (IL-1β), IL-2, IL-4, IL-5, IL-6, IL-7, IL-8, IL-10, IL-12, IL-3, IL-17A, granulocyte colony-stimulating factor (GCSF), interferon gamma (IFN-γ), vascular endothelial growth factor (VEGF), c-reactive protein (CRP), and tumor necrosis factor alpha (TNF-α). Without wishing to be bound by the theory, it is believed that acoustic waves delivered to cells (e.g., neuronal cell bodies or their axonal projections) or organs stimulate one or more processes that can up- or down-regulate production of cytokines and/or other factors.

A method of modulating a patient's immune system can include applying an ultrasonic transducer device, for example, as described herein, to the patient's skin overlaying a target site within the patient's body. Those of skill in the art will appreciate that various areas within a patient's body can be targeted by applying an ultrasonic transducer device, for example, as described herein, on skin overlaying the target site. In non-limiting embodiments or aspects, the target site is the patient's spleen. With regard to targeting, for example, in order to target a human patient's spleen, a device can be applied to the patient's skin between the ninth and eleventh ribs, optionally, between the ninth and tenth ribs and/or between the tenth and eleventh ribs.

In non-limiting embodiments or aspects, the patient to whom the acoustic waves are delivered has one or more conditions, ailments, diseases, or infections. In non-limiting embodiments or aspects, the patient has an autoimmune disease. In non-limiting embodiments or aspects, the patient has arthritis. In non-limiting embodiments or aspects, the patient has osteoarthritis and/or rheumatoid arthritis. In non-limiting embodiments or aspects, the patient has an injury to an organ, such as the kidney, and the acoustic waves are optionally targeted to the kidney. In non-limiting embodiments or aspects, the patient has acute respiratory distress syndrome (ARDS). In non-limiting embodiments or aspects, the patient has a bacterial, viral, and/or fungal infection. In non-limiting embodiments or aspects, the patient has sepsis. In non-limiting embodiments or aspects, the patient has a viral infection, and the virus is a coronavirus. In non-limiting embodiments or aspects, the patient has a viral infection, and the virus is SARS-CoV-2.

Once applied to the patient's skin, the device can be activated to deliver a plurality of acoustic waves to the target site, with parameters as described herein. As described above, a transducer device can include an array of transducers, which can be controlled by a processor to deliver acoustic waves at varying frequencies, negative acoustic pressure amplitudes, spatial peak average intensities, duty cycles, and/or durations, and these acoustic waves can be made up of one of more pulses. Useful ranges for the parameters of the acoustic waves can include a frequency of about 10 kHz to about 100 MHz, about 30 kHz to about 10 MHz, about 50 kHz to about 2 MHz, about 50 kHz to about 2 MHz, about 200 kHz to about 2 MHz, and/or about 400 kHz to about 500 kHz, a peak negative acoustic pressure amplitude of about 1 kPa to about 100 MPa, about 10 kPa to about 50 MPa, and/or about 100 kPa to about 10 MPa, a spatial peak average intensity of about 100 W/cm$^2$ to about 2,000 W/cm$^2$, a duty cycle of about 0.01% to about 100%, about 0.01% to about 75%, and/or about 0.01% to about 60%, and/or a duration of about 10 seconds to about 10 hours, about 1 minute to about 1 hour, about 3 minutes to about 30 minutes, about 3 minutes to about 20 minutes, about 5 minutes to about 20 minutes, and/or about 9 minutes to about 20 minutes, all values and subranges therebetween inclusive. As used herein, the term "about" means a stated value±10%.

In non-limiting embodiments or aspects, pulses making up an acoustic wave can have a pulse repetition frequency of about 10 Hz to about 5 kHz, about 20 Hz to about 2 kHz, and/or about 25 Hz to about 1 kHz, all values and subranges therebetween inclusive. In non-limiting embodiments or aspects, the pulses can have a pulse width of about 1 µs to 500 ms, about 5 µs to about 250 ms, and/or about 10 µs to about 200 ms, all values and subranges therebetween inclusive. In non-limiting embodiments or aspects, the pulses can have a cycle to pulse width ratio of about 1 to about 1000, about 2 to about 750, and/or about 5 to about 500, all values and subranges therebetween inclusive. In non-limiting embodiments or aspects, the pulses can be delivered with a bandwidth of about 1% to about 90%, about 1% to about 80%, and/or about 1% to about 70% of the peak frequency, all values and subranges therebetween inclusive. In non-limiting embodiments or aspects, the pulses can be delivered with a peak frequency of about 10 kHz to about 100 MHz, about 30 kHz to about 10 MHz, about 50 kHz to about 7 MHz, and/or about 50 kHz to about 5 MHz, all values and subranges therebetween inclusive.

In non-limiting embodiments or aspects, the acoustic waves can be delivered continuously (e.g., a duty cycle of 100%). In non-limiting embodiments or aspects, the acoustic waves can be delivered intermittently (e.g., a duty cycle of less than 100%), in one or more periods. In non-limiting embodiments or aspects, the acoustic waves are delivered intermittently in one or more periods, and the waves are delivered within one period with the same parameters, or different parameters as waves within one or more other periods. In non-limiting embodiments or aspects, the acoustic waves can be delivered for a duration (e.g., per period or total duration) of about 10 seconds to about 10 hours, about 1 minute to about 1 hour, about 3 minutes to about 30 minutes, about 3 minutes to about 20 minutes, about 5 minutes to about 20 minutes, and/or about 9 minutes to about 20 minutes, all values and subranges therebetween inclusive.

As described above, a device useful for the methods described herein can be one including a processor that is capable of controlling the output of the ultrasonic transducer device, for example, to provide automated changes to one or more parameters including frequency, negative acoustic pressure amplitude, spatial peak average intensity, duty cycle, duration, and/or steering angle. As also described above, a device useful for the methods described herein can include one or more ultrasonic transducers configured to receive acoustic feedback and convert that feedback to electrical signals. Those electrical signals can then be transmitted to the processor to determine whether there are one or more obstructions between the ultrasonic transducer device and the target site, for example, based on acoustically-mismatched materials within the body (e.g., bone). Non-limiting examples of such obstructions include bones, such as rib bones, the spine, and/or the sternum. The processor can then modify output of one or more of the ultrasonic transducers, for example, by adjusting a steering angle of the acoustic wave(s), to account for the one or more obstructions. In this way, the device, even if applied imprecisely to the patient's skin, can nevertheless deliver therapeutically-useful acoustic waves, for example, as a focused beam, to the target site.

EXAMPLE

A pre-clinical experiment was conducted to show proof-of-concept of the above-described methods. 20, six-week-old C57BL/6JNarl mice were divided into four groups, a control group (n=4) that received no challenge or intervention, a group that received ultrasound treatment (n=4), a group that received an intraperitoneal injection of 15 mg/kg lipopolysaccharide (LPS) (Sigma-Aldrich, St. Louis MO) (n=6), and a group that received LPS and ultrasound treatment (n=6). LPS challenge is a standard means for evaluating anti-inflammatory treatments. The experimental protocol is shown in FIG. 9. Ultrasound treatment was delivered for 20 minutes per day one day prior to LPS challenge, on the day of LPS challenge (immediately preceding the injection), and then daily for the following six days. Blood serum was collected prior to LPS challenge, and then 1, 6, and 24 hours following the challenge. Blood collections occurred prior to ultrasound treatment.

Ultrasound treatment was delivered with a 64-channel phased array system (SecondWave, State College PA), which was attached to the mice and focused on the animals' spleen, as shown schematically in FIG. 10. Treatment was delivered through an 8×8 GMP array designed for operation at 400-500 kHz frequency. Blood serum was collected 24 hours before the treatment, 1 hour following LPS challenge, 6 hours following LPS challenge, and 24 hours following LPS challenge. The pro-inflammatory cytokines IL-1β, IL-6, and TNF-α were selected for evaluation as those are believed to be involved in the cytokine storm induced by infection with SARS-CoV-2. Cytokine levels were assessed using an enzyme-linked immunosorbent assay (ELISA; BioLegend, San Diego CA).

Figure 11:
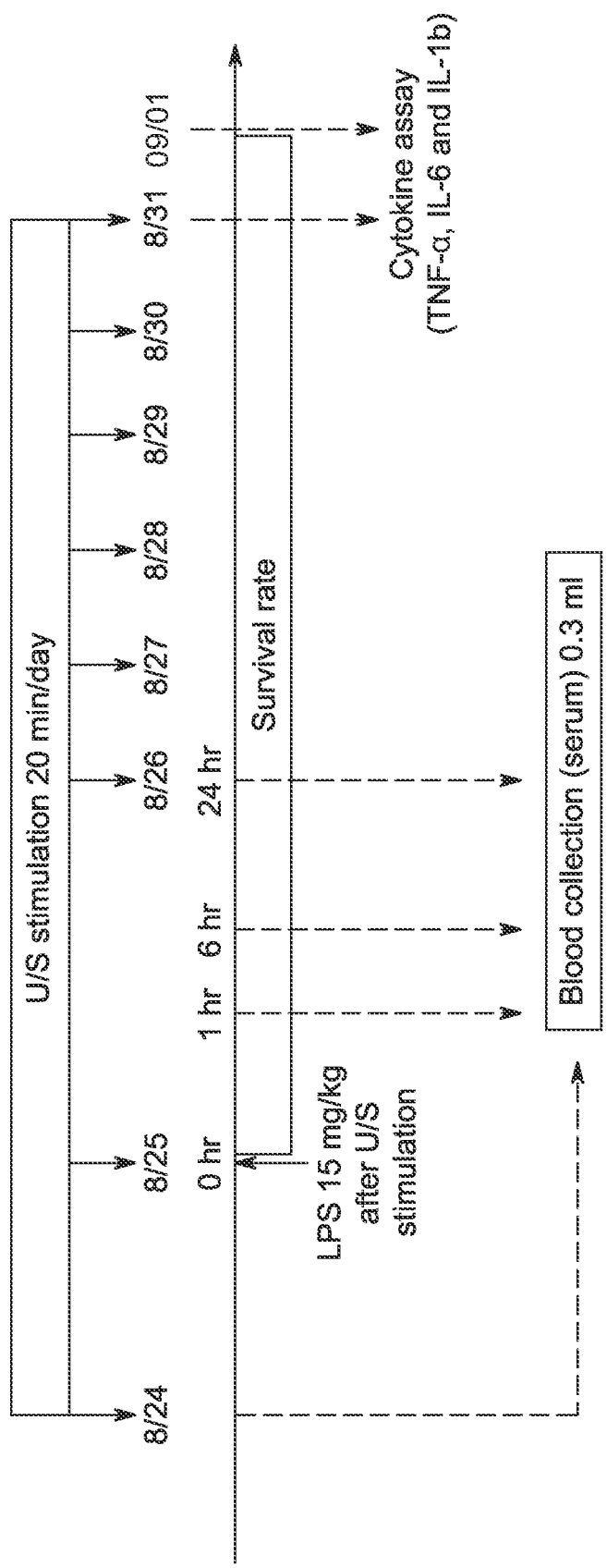
FIG. 11 is a diagram showing a timeline of a pre-clinical experiment using a non-limiting embodiment of a modulation device as described herein.
Figure 12:
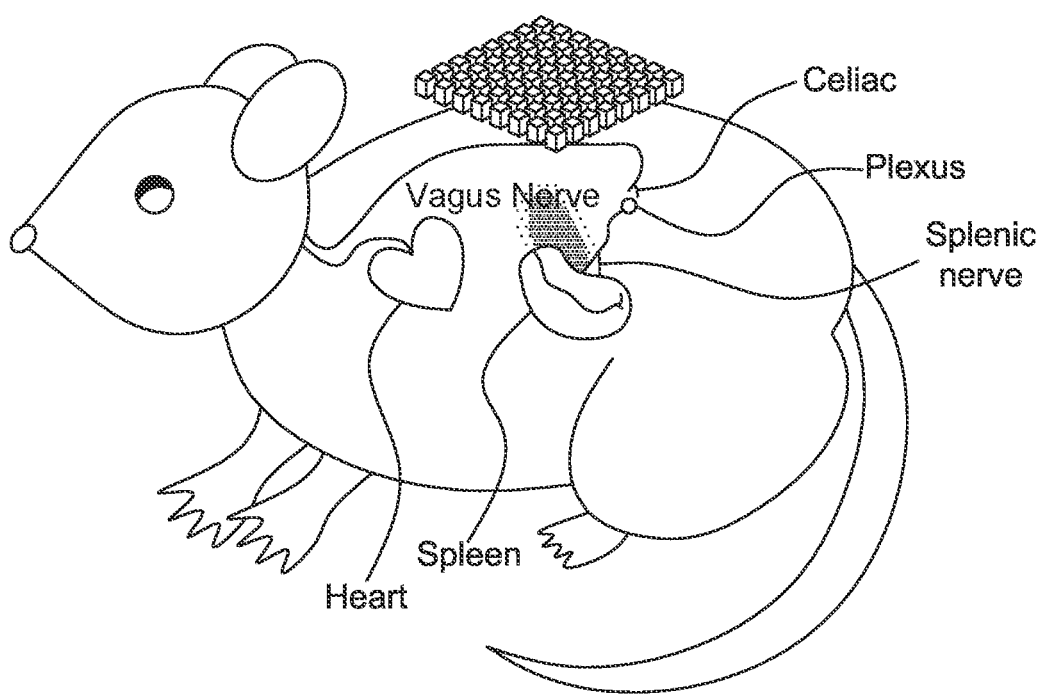
FIG. 12 is a schematic representation of a non-limiting embodiment of a device as described herein attached to a mouse.
Figure 13:
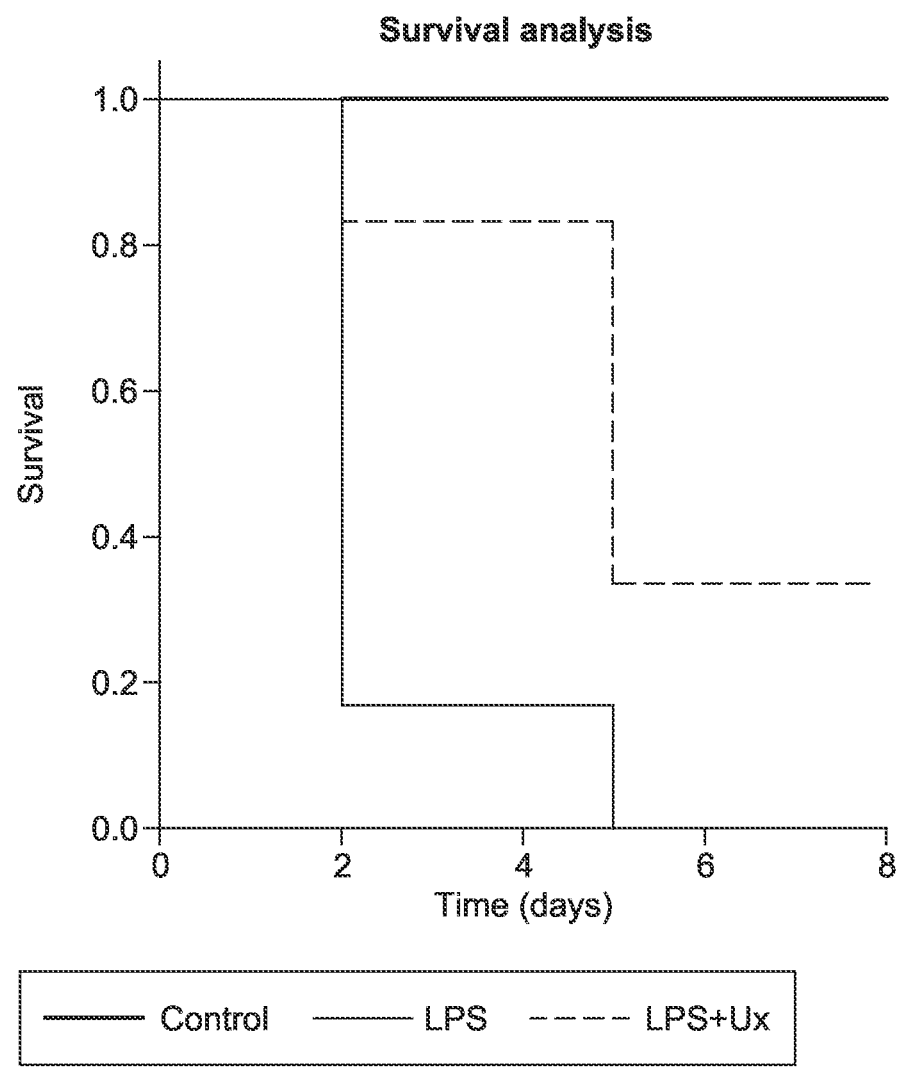
FIG. 13 is a graph showing results of a pre-clinical experiment in terms of survival of mice challenged with lipopolysaccharide (LPS)
Figure 14:
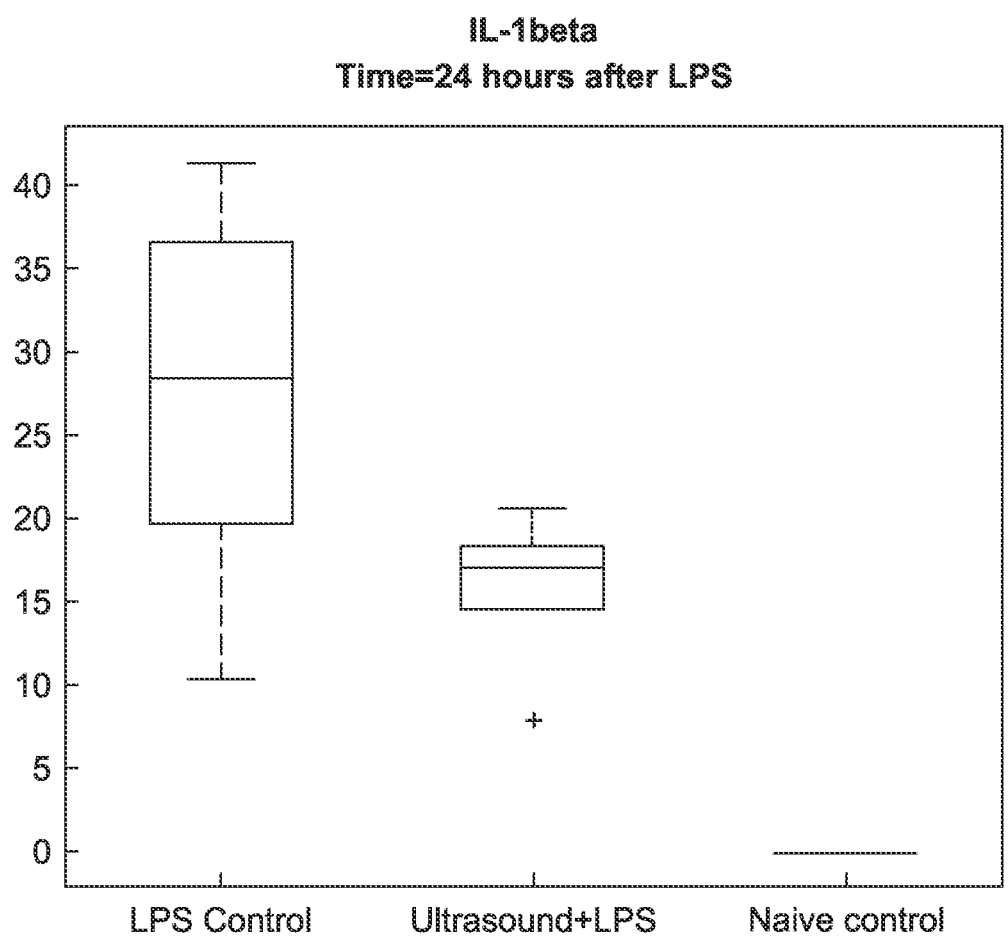
FIG. 14 is a boxplot showing results of a pre-clinical experiment in terms of the effect of treatment with a non-limiting embodiment of a device as described herein on cytokine levels in mice challenged with LPS.
Figure 15:
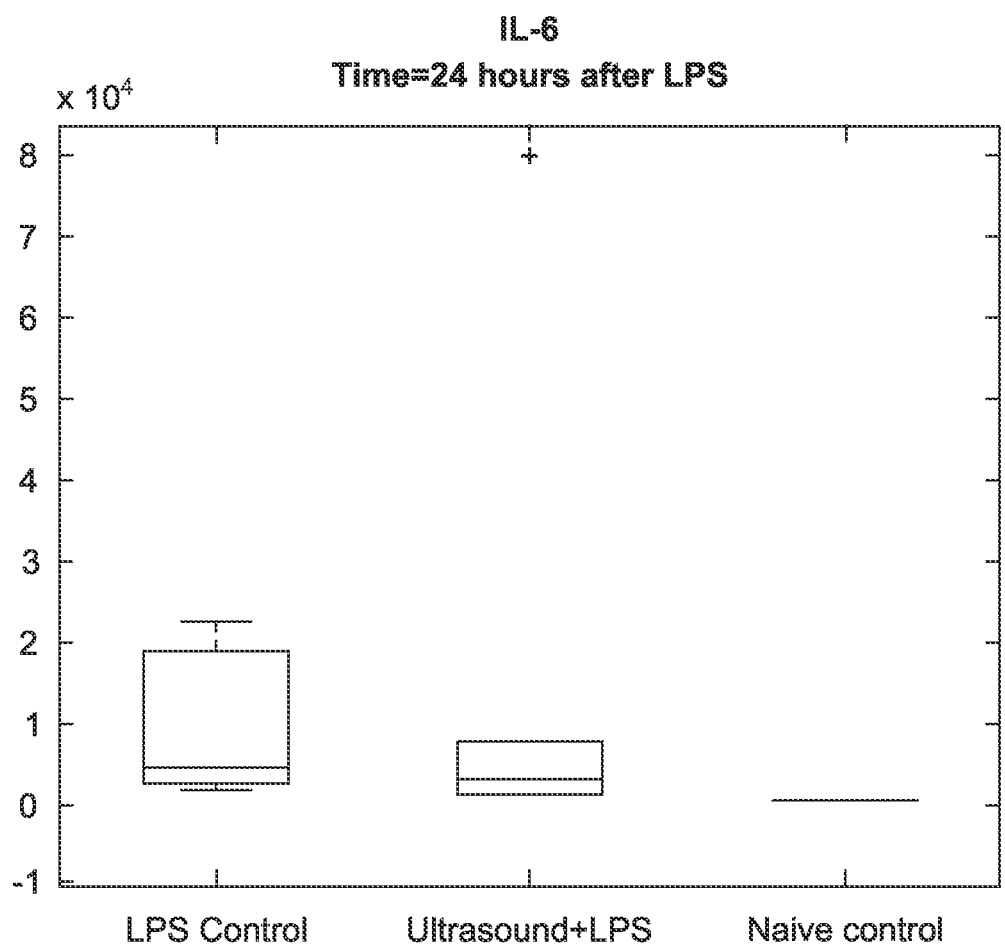
FIG. 15 is a boxplot showing results of a pre-clinical experiment in terms of the effect of treatment with a non-limiting embodiment of a device as described herein on cytokine levels in mice challenged with LPS.
Figure 16:
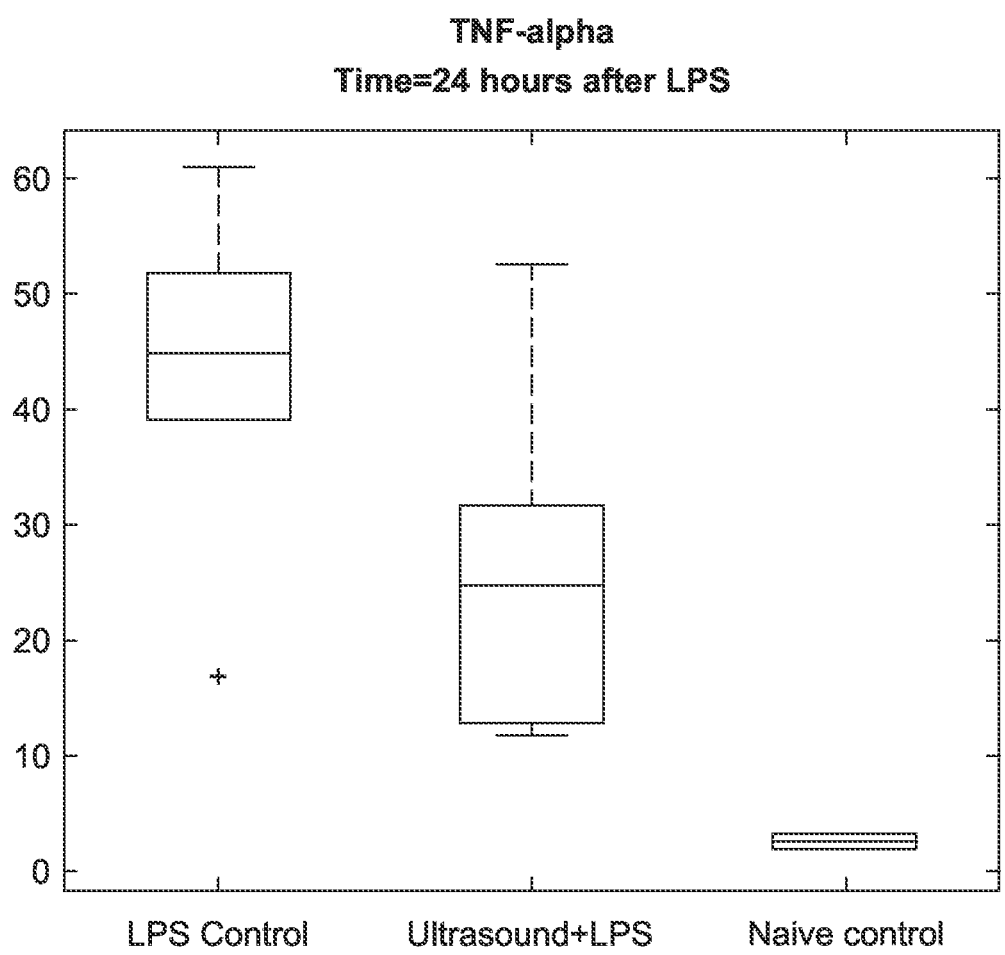
FIG. 16 is a boxplot showing results of a pre-clinical experiment in terms of the effect of treatment with a non-limiting embodiment of a device as described herein on cytokine levels in mice challenged with LPS.

Results of the experiment are shown in FIGS. 11-14. As can be seen in FIG. 11, ultrasound treatment significantly increased survival of mice challenged with an LPS injection. Of the six mice who received LPS, but who did not receive ultrasound treatment, five were deceased two days after LPS challenge, while no animals survived beyond five days post-challenge. In contrast, in the group that received ultrasound treatment, five of the six mice survived until day 5 post-LPS challenge, and two survived beyond that five-day time point. Further, as shown in FIGS. 12-14, levels of the pro-inflammatory cytokines of interest were decreased in the animals who received ultrasound treatment compared to those animals who received LPS challenge but no ultrasound treatment. The results of the above experiment show that ultrasound therapy can modulate levels of three important cytokines.

Although the above methods, systems, and computer program products have been described in detail for the purpose of illustration based on what is currently considered to be the most practical and preferred embodiments or aspects, it is to be understood that such detail is solely for that purpose and that the present disclosure is not limited to the described embodiments or aspects but, on the contrary, is intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect.

What is claimed is:

1. A device comprising:
   at least one first transducer device, wherein the at least one first transducer device comprises a material, wherein the material comprises:
      lead zirconate titanate (PZT);
      polyvinylidene difluoride (PVDF);
      aluminum nitride (AlN);
      scandium (Sc) doped AlN; or
      any combination thereof;
   wherein the at least one first transducer device comprises:
      a gas matrix piezoelectric (GMP) array; or
      a piezoelectric micromachined ultrasound transducer (pMUT) array; and
   at least one beam-forming processor programmed or configured to:
      cause the at least one first transducer device to produce a first acoustic wave, wherein the first acoustic wave comprises a plurality of pulses having a pulse repetition frequency, wherein a pulse width of each pulse of the plurality of pulses is in a range of 10 ns to 10 µs, and wherein the pulse repetition frequency is in a range of 1 Hz to 50 Hz;
      receive data associated with a second acoustic wave via a second transducer device, wherein the second transducer device comprises a detection transducer device that is configured to receive an acoustic wave that is a reflection of an acoustic wave provided by the at least one first transducer device and provides data associated with the reflection of the acoustic wave, and wherein the second acoustic wave is a reflection of the first acoustic wave;
      determine a characteristic of the second acoustic wave, wherein, when determining the characteristic of the second acoustic wave, the at least one beam-forming processor is programmed or configured to:
         determine a phase delay between the first acoustic wave and the second acoustic wave, where the phase delay is a difference in time between the first acoustic wave and the second acoustic wave;
         determine an amplitude of the second acoustic wave; and
         determine whether the amplitude of the second acoustic wave satisfies a threshold; and
      determine whether to change a beam path of an acoustic wave produced by the at least one first transducer device based on the characteristic of the second acoustic wave, wherein, when determining whether to change the beam path of an acoustic wave produced by the at least one first transducer device, the at least one beam-forming processor is programmed or configured to:
         determine to change the beam path of an acoustic wave produced by the at least one first transducer device from the beam path of the first acoustic wave based on the characteristic of the second acoustic wave.

2. The device of claim 1, wherein the first acoustic wave has a bandwidth of 20% to 150% of peak frequency, wherein the peak frequency is a range of 50 kHz to 5 MHz;
   wherein a number of cycles per pulse width of a pulse of the first acoustic wave is in a range of 1 to 5;
   wherein the at least one beam-forming processor is further programmed or configured to:
      cause the at least one first transducer device to produce a third acoustic wave along the beam path based on causing the at least one first transducer device to change the beam path of an acoustic wave produced by the at least one first transducer device, wherein the third acoustic wave comprises a plurality of pulses having a pulse repetition frequency, wherein each pulse has a pulse width in a range of 1 us to 500 ms, and wherein the pulse repetition frequency is in a range of 25 Hz to 1000 Hz;
   wherein the third acoustic wave has a bandwidth of 1-70% of peak frequency, wherein the peak frequency is a range of 50 kHz to 5 MHz; and
   wherein a number of cycles per pulse width of a pulse of the third acoustic wave is in a range of 5 to 2,500,000.

3. The device of claim 1, further comprising:
   the second transducer device.

4. The device of claim 1, wherein the at least one beam-forming processor is further programmed or configured to:
   provide an indication based on the characteristic of the second acoustic wave;
   wherein the indication comprises at least one of:
      an indication associated with discontinuing a treatment,
      an indication associated with improper placement of the at least one first transducer device, an indication associated with a prompt for receiving a user input, or any combination thereof.

5. The device of claim 1, wherein, the at least one beam-forming processor is further programmed or configured to:
  determine an amount of change to be made to the beam path of an acoustic wave produced by the at least one first transducer device from the beam path of the first acoustic wave based on the characteristic of the second acoustic wave, or
  determine that no amount of change is to be made to the beam path of an acoustic wave produced by the at least one first transducer device from the beam path of the first acoustic wave based on the characteristic of the second acoustic wave.

6. The device of claim 5, wherein the at least one beam-forming processor is further programmed or configured to:
  cause the at least one first transducer device to change the beam path of an acoustic wave produced by the at least one first transducer device based on the amount of change of the beam path of an acoustic wave produced by the at least one first transducer device from the beam path of the first acoustic wave.

7. The device of claim 1, wherein, the at least one beam-forming processor is further programmed or configured to:
  determine an amount of change to be made to the beam path of an acoustic wave produced by the at least one transducer device from the beam path of the first acoustic wave based on the characteristic of the second acoustic wave; and
  wherein, when determining the amount of change of the beam path of an acoustic wave produced by the at least one first transducer device from the beam path of the first acoustic wave, the at least one beam-forming processor is further programmed or configured to:
  determine the amount of change of the beam path of an acoustic wave produced by the at least one first transducer device from the beam path of the first acoustic wave based on the phase delay and determining that the amplitude of the second acoustic wave satisfies the threshold.

8. The device of claim 1, wherein the at least one beam-forming processor is further programmed or configured to:
  cause the at least one first transducer device to deliver a plurality of acoustic waves to a target site within a patient's body, thereby modulating the patient's immune system, wherein the target site is the patient's spleen.

9. A method comprising:
  causing, with at least one beam-forming processor, at least one transducer device to produce a first acoustic wave, wherein the first acoustic wave comprises a plurality of pulses having a pulse repetition frequency, wherein a pulse width of each pulse of the plurality of pulses is in a range of 10 ns to 10 µs, and wherein the pulse repetition frequency is in a range of 1 Hz to 50 Hz;
  receiving, with the at least one beam-forming processor, data associated with a second acoustic wave, wherein the second acoustic wave is an acoustic wave that is a reflection of the first acoustic wave;
  determining, with the at least one beam-forming processor, a characteristic of the second acoustic wave, wherein determining the characteristic of the second acoustic wave comprises:
    determining a phase delay between the first acoustic wave and the second acoustic wave, where the phase delay is a difference in time between the first acoustic wave and the second acoustic wave;
    determining an amplitude of the second acoustic wave;
    determining whether the amplitude of the second acoustic wave satisfies a threshold; and
  determining, with the at least one beam-forming processor, whether to change a beam path of an acoustic wave produced by the at least one first transducer device based on the characteristic of the second acoustic wave, wherein determining whether to change the beam path of an acoustic wave produced by the at least one first transducer device comprises:
    determining to change the beam path of an acoustic wave produced by the at least one first transducer device from the beam path of the first acoustic wave based on the characteristic of the second acoustic wave.

10. The method of claim 9, further comprising:
providing an indication based on the characteristic of the second acoustic wave;
wherein the indication comprises at least one of:
  an indication associated with discontinuing a treatment,
  an indication associated with improper placement of the at least one first transducer device,
  an indication associated with a prompt for receiving a user input, or
  any combination thereof.

11. The method of claim 9, further comprising:
determining an amount of change to be made to the beam path of an acoustic wave produced by the at least one first transducer device from the beam path of the first acoustic wave based on the characteristic of the second acoustic wave, or
determining that no amount of change is to be made to the beam path of an acoustic wave produced by the at least one first transducer device from the beam path of the first acoustic wave based on the characteristic of the second acoustic wave.

12. The method of claim 11, further comprising:
causing the at least one first transducer device to change the beam path of an acoustic wave produced by the at least one first transducer device based on the amount of change of the beam path of an acoustic wave produced by the at least one first transducer device from the beam path of the first acoustic wave.

13. The method of claim 9, further comprising:
determining an amount of change to be made to the beam path of an acoustic wave produced by the at least one transducer device from the beam path of the first acoustic wave based on the characteristic of the second acoustic wave;
wherein determining the amount of change of the beam path of an acoustic wave produced by the at least one first transducer device from the beam path of the first acoustic wave comprises:
  determining the amount of change of the beam path of an acoustic wave produced by the at least one first transducer device from the beam path of the first acoustic wave based on the phase delay and determining that the amplitude of the second acoustic wave satisfies the threshold.

14. The method of claim 9, further comprising:
delivering, with the at least one first transducer device, a plurality of acoustic waves to a target site within a patient's body, thereby modulating the patient's immune system, wherein the target site is the patient's spleen.

15. A non-transitory computer-readable medium including one or more instructions that, when executed by at least one beam-forming processor, cause the at least one beam-forming processor to:
cause at least one first transducer device to produce a first acoustic wave, wherein the first acoustic wave comprises a plurality of pulses having a pulse repetition frequency, wherein a pulse width of each pulse of the plurality of pulses is in a range of 10 ns to 10 µs, and wherein the pulse repetition frequency is in a range 1 Hz to 50 Hz;
receive data associated with a second acoustic wave via a second transducer device, wherein the second transducer device comprises a detection transducer device that is configured to receive an acoustic wave that is a reflection of an acoustic wave provided by the at least one first transducer device and provides data associated with the reflection of the acoustic wave, and wherein the second acoustic wave is a reflection of the first acoustic wave;
determine a characteristic of the second acoustic wave, wherein, the one or more instructions that cause the at least one beam-forming processor to determine the characteristic of the second acoustic wave, cause the at least one beam-forming processor to:
determine a phase delay between the first acoustic wave and the second acoustic wave, wherein the phase delay is a difference in time between the first acoustic wave and the second acoustic wave;
determine an amplitude of the second acoustic wave; and
determine whether the amplitude of the second acoustic wave satisfies a threshold; and
determine whether to change a beam path of an acoustic wave produced by the at least one first transducer device based on the characteristic of the second acoustic wave, wherein, when determining whether to change the beam path of an acoustic wave produced by the at least one first transducer device, the at least one beam-forming processor is programmed or configured to:
determine to change the beam path of an acoustic wave produced by the at least one first transducer device from the beam path of the first acoustic wave based on the characteristic of the second acoustic wave.

16. The non-transitory computer-readable medium of claim 15, wherein the one or more instructions further cause the at least one beam-forming processor to:
provide an indication based on the characteristic of the second acoustic wave; and
wherein the indication comprises at least one of:
an indication associated with discontinuing a treatment,
an indication associated with improper placement of the at least one first transducer device,
an indication associated with a prompt for receiving a user input, or
any combination thereof.

17. The non-transitory computer-readable medium of claim 15, wherein, the one or more instructions further cause the at least one beam-forming processor to:
determine an amount of change to be made to the beam path of an acoustic wave produced by the at least one transducer device from the beam path of the first acoustic wave based on the characteristic of the second acoustic wave; and
wherein, the one or more instructions that cause the at least one beam-forming processor to determine the amount of change of the beam path of an acoustic wave produced by the at least one first transducer device from the beam path of the first acoustic wave, cause the at least one beam-forming processor to:
determine the amount of change of the beam path of an acoustic wave produced by the at least one first transducer device from the beam path of the first acoustic wave based on the phase delay and determining that the amplitude of the second acoustic wave satisfies the threshold.

18. The non-transitory computer-readable medium of claim 15, wherein, the one or more instructions further cause the at least one beam-forming processor to:
determine an amount of change to be made to the beam path of an acoustic wave produced by the at least one transducer device from the beam path of the first acoustic wave based on the characteristic of the second acoustic wave; and
cause the at least one first transducer device to change the beam path of an acoustic wave produced by the at least one first transducer device based on the amount of change of the beam path of an acoustic wave produced by the at least one first transducer device from the beam path of the first acoustic wave.

* * * * *